(12) United States Patent
Burba et al.

(10) Patent No.: US 7,927,344 B2
(45) Date of Patent: Apr. 19, 2011

(54) EYE POSITIONER

(76) Inventors: Thomas A. Burba, Plymouth, MN (US); David R. Hardten, Orono, MN (US)

( * ) Notice: Subject to any disclaimer, the term of this patent is extended or adjusted under 35 U.S.C. 154(b) by 600 days.

(21) Appl. No.: 11/580,466

(22) Filed: Oct. 13, 2006

(65) Prior Publication Data

US 2008/0103367 A1    May 1, 2008

(51) Int. Cl.
*A61F 9/00* (2006.01)
(52) U.S. Cl. .................. 606/166; 623/6.12; 606/107
(58) Field of Classification Search .......... 606/166, 606/107; 623/5.11, 6.12
See application file for complete search history.

(56) References Cited

U.S. PATENT DOCUMENTS

| 5,009,660 A * | 4/1991 | Clapham ............. 606/166 |
| 6,436,133 B1 * | 8/2002 | Furst et al. ............ 623/1.15 |
| 2004/0225284 A1 * | 11/2004 | Webb et al. ........... 606/5 |

* cited by examiner

*Primary Examiner* — (Jackie) Tan-Uyen T Ho
*Assistant Examiner* — Jonathan W Miles
(74) *Attorney, Agent, or Firm* — Hugh D. Jaeger

(57) ABSTRACT

Self-contained eye positioner having an annular vacuum ring composed of a channeled support ring and an overmolded flexible sealing ring having an attached rigid hollow tube secured to a syringe by use of an attachment fixture. The syringe, which also functions as a handle, provides a vacuum source, the vacuum of which is communicated to the annular vacuum ring to suctionally adhere the annular vacuum ring to the eyeball for maneuvering thereof. Accompanying closely associated auxiliary devices are provided for use with the eye positioner. No external vacuum source is required.

13 Claims, 31 Drawing Sheets

EYE POSITIONER

CROSS REFERENCES TO RELATED APPLICATIONS

This application is related to patent application Ser. No. 09/664,464 filed Sep. 18, 2000, entitled "Eye Positioner", now U.S. Pat. No. 6,436,113.

BACKGROUND OF THE INVENTION

1. Field of the Invention

The present invention is for an ophthalmic instrument, and more particularly, pertains to an eye positioner which can be utilized for positioning, manipulating, and fixating the eye during opthalmology surgery, eye exams, refractive surgery, and laser treatment. It can be used in various types of refractive surgery such as PRK, LASIK, Holmium:YAG Thermokeratoplasty, various ophthalmic laser treatments such as YAG, femto second laser, dye laser, photocoagulation using various laser wavelengths, intracorneal ring insertion and removal, incisional keratotomy, ophthalmic exams, corneal surgery, and foreign body removal.

2. Description of the Prior Art

Prior art eye fixation hand pieces are used by surgeons for engaging and holding an eye at a fixed reference position during eye surgery. Some of these hand pieces, such as the Thornton fixation ring, engage the eye with teeth or serrated edges. Others, such as the one shown in Krasner, U.S. Pat. No. 4,796,623, suggest a vacuum attachment to the eye, but painfully deform the eye between ridges. Vacuum attachment of an eye fixation device is also suggested in FIG. 2 of L'Esperance, U.S. Pat. No. 4,718,418, and in O'Dell, U.S. Pat. No. 4,558,698; but these are not hand pieces.

One device that has been proposed for use in fixating the eye of a patient is shown in Clapham, U.S. Pat. No. 5,009,660. The Clapham device utilizes a vacuum ring and purging gas system at the end of a handle which extends away from the vacuum ring handle at an angle. The vacuum ring can be secured to the eye around the cornea. The purging system is for dispersing evaporated tissue. A gas purging eye fixation hand piece includes a vacuum ring evacuated by a suction line through a handle via connection to a vacuum pump, by which a purging gas is delivered to an array of purging nozzles aimed into the vacuum ring from around an inner perimeter of the vacuum ring to direct purging gas jets toward the proximal side of the vacuum ring attached to an eye that is held steady in a reference position for laser surgery. A preferably disposable and resilient eye-engaging ring is removably mounted on the vacuum ring to engage the eye around the cornea, and a spring-biased suction release valve is preferably mounted on the hand piece handle for finger operation by the surgeon to release the hand piece from the eye when surgery is completed. Mounting of gas purging nozzles on the hand piece automatically positions them properly for keeping the cornea clear of particles formed by laser ablation of eye tissue, once the hand piece is properly fixed to the eye.

L'Esperance, U.S. Pat. No. 4,718,418, uses a vacuum ring which can be placed on the eye, but the vacuum ring is rigidly connected to an external piece of equipment (in this case, a laser used in treatment of the eye). This technique has inherent dangers, however, in that if the patient should panic or for whatever reason attempt to move away from the rigid device, serious trauma to the eye can result.

Eye Fixation Speculum, U.S. Pat. No. 5,171,254, describes an ophthalmic instrument for fixating a patient's eye during an ophthalmic procedure. The instrument includes a speculum securable against the patient's bony orbit, and a fixation ring attachable to the patient's eye, the ring including both a mechanism for fixating the ring with respect to the eye and a mechanism for adjustably attaching the ring to the speculum. The instrument may include one or more bubble-type levels carried on the fixation ring for indicating the orientation of the ring and assisting the surgeon in orienting the eye of the patient before securing the ring to the speculum. Other devices are used with incisional devices attached to vacuum rings for RK (radial keratotomy) and with trephines, all having tubing and external vacuum sources.

Currently, ophthalmologists often merely use a pair of forceps or a metal ring to stabilize the eye during such procedures. Obviously, this can be less than satisfactory, as it can be difficult to get a secure grip on the eyeball. Squeezing the eye with the forceps can elevate intraocular pressure and deform the shape of the cornea, inducing astigmatism. The most frequently used method is to ask the patient to keep his eye immobilized by fixating on an illuminated target. This is very difficult for most patients during excimer laser surgery, especially when the eyelids are being held open by a speculum and distracting noises are produced by the high energy laser striking the cornea. In radial keratotomy (RK), it is extremely important for the patient to hold the eye absolutely still when the multiple incisions of the cornea are made with the diamond scalpel or serious complications could occur. The other available fixation method is to use a pair of forceps (similar to tweezers) and firmly grasp the white portion of the eye. This is also an unsatisfactory method which causes pain for the patient and distorts the eye.

The Thornton ring consists of either a partial or complete circular ring with a series of teeth for gripping the eye at the sclera (white area) and a handle protruding at an angle from the ring. The instrument, due to the ring teeth, is painful for the patient because the anesthetic is only effective for the cornea and does not completely penetrate and anesthetize the sclera.

Forceps, a tweezers-type instrument, are also painful as they are used to grasp the eye at the sclera by pinching, which often causes a hemorrhage. The cornea shape easily becomes distorted, inducing astigmatism, and the intraocular pressure rises unpredictably. Forceps have a numbers of drawbacks including subconjunctival hemorrhage and pain which can cause increased patient anxiety. Disadvantages can include torsion movements when a patient tries to move an eye with one point fixation and the resultant movement is incyclo or excyclotorsion. Depending on the degree of pressure exerted by the surgeon, the intraocular pressure can fluctuate greatly. In RK, the depth of each incision may vary depending on the intraocular pressure, and surgeons will try to maintain a constant intraocular pressure by altering the forceps pressure on the eye. Corneal distortion also occurs depending on the force exerted and distance from the cornea of the forceps. It is not completely understood how altering the corneal shape intraoperatively during RK, LASIK and PRK affects the outcome. The use of various rings with multiple small teeth, such as the Thornton ring, eliminates some of the problems with one-point fixation. However, all these methods have several drawbacks.

Some prior art devices, including ring structures and a tubular component connected thereto, were problematic in that the connection between the ring structures and the tubular component was of secondary consideration and of barely adequate construction. Often, the connection therebetween was not entirely suitable with respect to a solid pressure or vacuum connection, or the stability of the ring structures with respect to the tubular component was not entirely satisfactory.

The present invention provides an eye positioner which provides for excellent pressure or vacuum connections and which provides for suitable accommodation and connection of a tubular component to the ring structure by the use of the attachment fixture.

Some prior art devices included ring structures formed of a rigid support ring having an annular channel which accommodated a flexible sealing ring affixed therein by frictional engagement, adhesive, or a combination thereof. As such, the attachment of the rigid support ring to the flexible sealing ring may have been of secondary consideration. Such connections were not entirely suitable, particularly when an adhesive bond may not have been evenly applied, resulting in nonlinear geometry, irregular structure, and the like. The present invention overcomes the inadequacies of the prior art by providing an annular vacuum ring in which a flexible sealing ring is overmolded onto a channeled support ring.

The invention also ensures that any modest change in the intraocular pressure of the eye is both controlled and predictable, unlike the prior art methods (such as grasping the eye with a forceps) which can induce erratic changes in intraocular pressure and concomitant distortion of the corneal topography.

The instrument of the invention also eliminates the problems encountered due to patient eye movement during exams and ophthalmic surgery.

SUMMARY OF THE INVENTION

The general purpose of the present invention is to position and stabilize the eye during various ophthalmic procedures and examinations. It is necessary during refractive surgery, such as PRK, LASIK, Holmium: YAG Thermokeratoplasty, ophthalmic laser treatment, such as YAG, dye laser, femto second laser, various types of photocoagulation, intracorneal ring insertion and removal, incisional keratotomy, ophthalmic exams, conductive keratoplasty, corneal surgery, and foreign body removal, that the eye can be moved to different locations and held in position during the procedure.

The eye positioner is a handheld instrument which can be provided in more than one closely related structure form in order to accommodate accompanying closely associated devices for use therewith. The surgeon can utilize the eye positioner to grasp, move and position the eye in any direction. The invention is formed, in part, by a flexible sealing ring mated, such as by overmolding, to a channeled support ring to form a unitary annular vacuum ring. Other components include a receptacle and other geometrically configured structure which extend from the channeled support ring, and a housing extending from the flexible sealing ring to combine and form an attachment fixture. A rigid hollow tube firmly affixes within the attachment fixture and extends therefrom to connect the annular vacuum ring with a vacuum source in the form of a syringe by the use of a Luer adapter. The annular vacuum ring is permanently attached at any desirable position to a rigid hollow tube, and thus to the syringe, during manufacturing. One important aspect of the instrument design is that the syringe, which is part of the self-contained eye positioning device, provides the vacuum source which is rigidly connected by the use of an attachment fixture to the annular vacuum ring, whereby the syringe can be utilized as an instrument handle, as can the rigid hollow tube. The vacuum level is controlled by the amount a plunger is extended and by the syringe capacity, which causes the vacuum ring to adhere to the eye. The syringe plunger may be spring-loaded to assist in the plunger retraction. The syringe then functions as an integral part of the invention serving as an instrument handle for positioning the annular vacuum ring about the surface of the eye. As the syringe plunger is extracted, vacuum is created and the annular vacuum ring adheres to the eye. The surgeon can then position or move the eye by utilizing the syringe barrel as the instrument handle. As the plunger is extracted further outward from the syringe, the vacuum level increases and the eye becomes more firm. The surgeon has control by hand to begin, increase, decrease, stop or release vacuum, and intraocular pressure is determined by the surgeon's use of the syringe plunger. The instrument does not need any external power vacuum source to be operational and can be used in any location where a power source is unavailable. The syringe can be of any suitable volume and may have a spring on the plunger to assist in retracting the plunger and creating vacuum. In the alternative, other vacuum sources and handle structures and various other arrangements can be utilized.

The device is a unitized instrument for positioning and fixating the eye. This instrument has an integral self-contained vacuum source supplied by a syringe in conjunction with an annular vacuum ring. The vacuum is supplied by a syringe and conduit to an annular vacuum ring which is placed concentrically around the cornea (typically, seating on the episclera). Once the vacuum ring is placed on the eye and vacuum is applied, the patient's eye can be moved or held in any suitable position. The annular vacuum ring, which includes a flexible sealing ring, has a hemostatic effect on any traumatized blood vessels of the eye and is an effective dam in isolating the cornea from any fluids and debris during a variety of corneal surgical procedures. This is particularly useful during the LASIK procedure. The handheld instrument of the invention is the only device to position an eye utilizing an integral vacuum source, a syringe, not requiring an external pump or power source for supplying vacuum, and a vacuum ring applied to the eye.

This is in contrast to other devices for manipulating and holding the eye, such as forceps and fixation rings, which rely on mechanical force in grasping and securing the eye for fixation and positioning. These devices can distort the eye and cause trauma and hemorrhage.

According to one embodiment of the present invention, there is provided an eye positioner including an attachment fixture, a syringe, the barrel of which is utilized as a handle, a syringe plunger shaft having a spring located along the shaft, a Luer adapter and a rigid hollow tube extending from the syringe, a flexible sealing ring preferably mated such as by overmolding to a channeled support ring to form a unitary annular vacuum ring, a receptacle extending from the channeled support ring, and an overmolded housing extending from the flexible sealing ring to matingly form an attachment fixture for secured and connected accommodation of one end of the rigid hollow tube extending from the syringe.

One significant aspect and feature of the present invention is an eye positioner which is completely self-contained.

Another significant aspect and feature of the present invention includes a hand operated syringe to provide vacuum to an annular vacuum ring.

Yet another significant aspect and feature of the present invention is that vacuum, at the annular vacuum ring, may be readily controlled by simply repositioning the plunger of the syringe.

Still another significant aspect and feature of the present invention is an eye positioner that offers total maneuverability of the eye and does not cause eye trauma.

An additional significant aspect and feature of the present invention is that the surgeon has control of vacuum level and eye movement.

A further significant aspect and feature of the present invention is that the device is easy to use, is handheld, and the eye can be positioned in multiple directions.

A still further significant aspect and feature of the present invention is the use of an annular sealing ring which has a number of advantages over rings which have small prongs or teeth, such as hemostasis from bleeding from corneal pannus which is common during LASIK, and allows an almost bloodless dissection of the pterygium from the corneal surface.

Still another significant aspect and feature of the present invention is that the device prevents cyclotorsion commonly seen when patients are placed in a supine position. Small amounts of rotation (5 to 10 degrees) can significantly reduce the effect of astigmatic correction during refractive surgery.

A significant aspect and feature of the present invention is a vacuum ring which acts as an effective dam to keep tears, blood, debris and other contaminates in the area of treatment away from the cornea during ophthalmic treatment.

A significant aspect and feature of the present invention is the use of a flexible sealing ring having arrays of eye contact rings.

Yet another significant aspect and feature of the present invention is the use of a channeled support ring in combination with an overmolded flexible sealing ring which unitarily forms an annular vacuum ring.

Yet another significant aspect and feature of the present invention is the use of annular open spaces within the central region of the annular vacuum ring to accommodate accompanying closely associated auxiliary devices.

Still another significant aspect and feature of the present invention is a receptacle extending from a channeled support ring which matingly accommodates an overmolded housing into an attachment fixture extending from the channeled support ring.

Still another significant aspect and feature of the present invention is the use of an attachment fixture for secured and connected accommodation of one end of a rigid hollow tube extending from a syringe.

Yet another significant aspect and feature of the present invention is an attachment fixture having an engagement channel and a connecting restrictive access channel formed by opposed stabilizer panels extending from opposed arcuate sections being flexibly associated to allow forcible accommodation of a rigid hollow tube to an attachment fixture.

Still another significant aspect and feature of the present invention is the use of an attachment fixture, whereby the structure and combination of multiple features includes forced frictional snap engagement of one end of a rigid hollow tube within an engagement channel located in the attachment fixture having opposed stabilizer panels located about a periphery of the engagement channel, the accommodation of one end of the rigid hollow tube within a bore in a housing, and an adhesive applied over and about said features combined to provide for a sturdy and well connected joining of the rigid hollow tube to the annular vacuum ring.

Yet another significant aspect and feature of the present invention is a second form of the eye positioner incorporating a channeled support ring having upwardly extending external threads for accommodation of accompanying closely associated auxiliary devices.

Still another significant aspect and feature of the present invention is the spacing of the syringe from the components constituting the general structure of the eye positioner by combinations of tubes, Luer connectors and a stopcock to provide operational advantages.

Still another significant aspect and feature of the present invention is the relocation of components to provide different handle combination schemes.

Still another significant aspect and feature of the present invention is the use of differently shaped lenses which can be readily installed within an eye positioner to change the shape of the eye for subsequent radiation and other procedures.

Still another significant aspect and feature of the present invention is the use of screw-on devices such as a reference ring, a planar surgical instrument guide, a domed surgical instrument guide, a controlled area guide, or an injection guide.

Having thus described embodiments and significant aspects and features of the present invention, it is the principal object of the present invention to provide an eye positioner.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
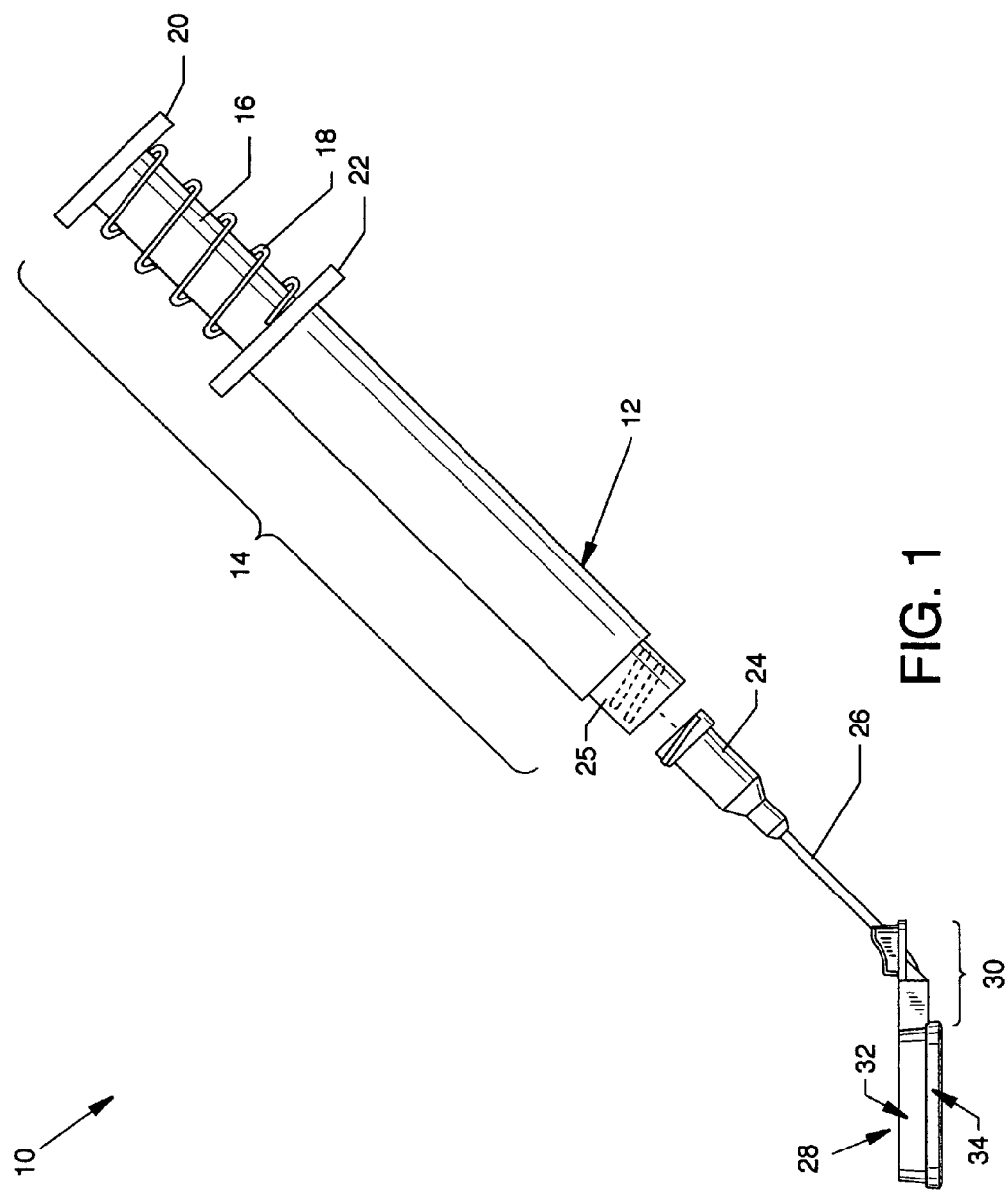
FIG. 1 is a semi-exploded side view of a first form of eye positioner, the present invention.

FIG. 1 is a semi-exploded side view of an eye positioner 10, the present invention in a first form, provided for use by itself or with accompanying closely associated devices, as described later in detail. Visible members of the eye positioner 10 include an instrument handle 12, being the barrel of a syringe 14, a syringe plunger shaft 16, a spring 18 located over and about the syringe plunger shaft 16 and between a syringe plunger shaft planar member 20 and an annular or other suitably shaped grasping tab 22 at one end of the syringe 14. One end of a Luer adapter 24 is accommodatingly secured at an internally threaded end 25 of the syringe 14 opposite the grasping tab 22. A rigid hollow tube 26 extends from one end of the Luer adapter 24 to secure and to communicate with an annular vacuum ring 28 by the use of an attachment fixture 30, the latter of which extends from the annular vacuum ring 28. Such an arrangement provides communication between the syringe 14 and the annular vacuum ring 28. The annular vacuum ring 28 is composed of a channeled support ring 32 and a flexible sealing ring 34 that engages and attaches such as by overmolding to the channeled support ring 32. Overmolding is a multimaterial process of two or more resins with uniquely different properties and seamlessly integrated and joined through the molding process into one molded component. This forms a chemical or adhesive bond between the substrate and second material. In the invention, the substrate is the channeled support ring 32 which is made in a first injection mold tool and which consists of hard and rigid plastic. The channeled support ring 32 is removed from the first injection mold tool and then placed in a second mold, i.e., an overmold tool, where CPT C-Flex or other suitable material is applied by injection molding to form the flexible sealing ring 34 which forms a chemical or adhesive bond with the channeled support ring 32. The overmold tool is cut to precisely fit the channeled support ring 32 in it, i.e., the substrate, and allow for application of CPT C-Flex overmold material, i.e., the overmold therein. The overmold and the substrate, i.e., the thermoplastic elastomer of the CPT C-Flex forming the flexible sealing ring 34 and the plastic forming the channeled support ring 32 form a chemical bond at their surface interface. The channeled support ring 32 preferably is formed of polypropylene, such as Pro-fax PDC polypropylene by the Basell Corporation, for example, but could be formed of any other suitable material embracing overmolding. The flexible sealing ring 34 preferably is formed of CPT C-flex R70-046, such as by the Consolidated Polymer Corporation, for example, but could be formed of any other suitable material embracing overmolding. Other methods of attachment of the flexible sealing ring 34 to the channeled support ring 32, such as by the use of adhesive, ultrasonic welding, or other suitable means, may be used as appropriate, and the use of overmolding shall not be deemed to be limiting to the scope of the invention.

Figure 2:
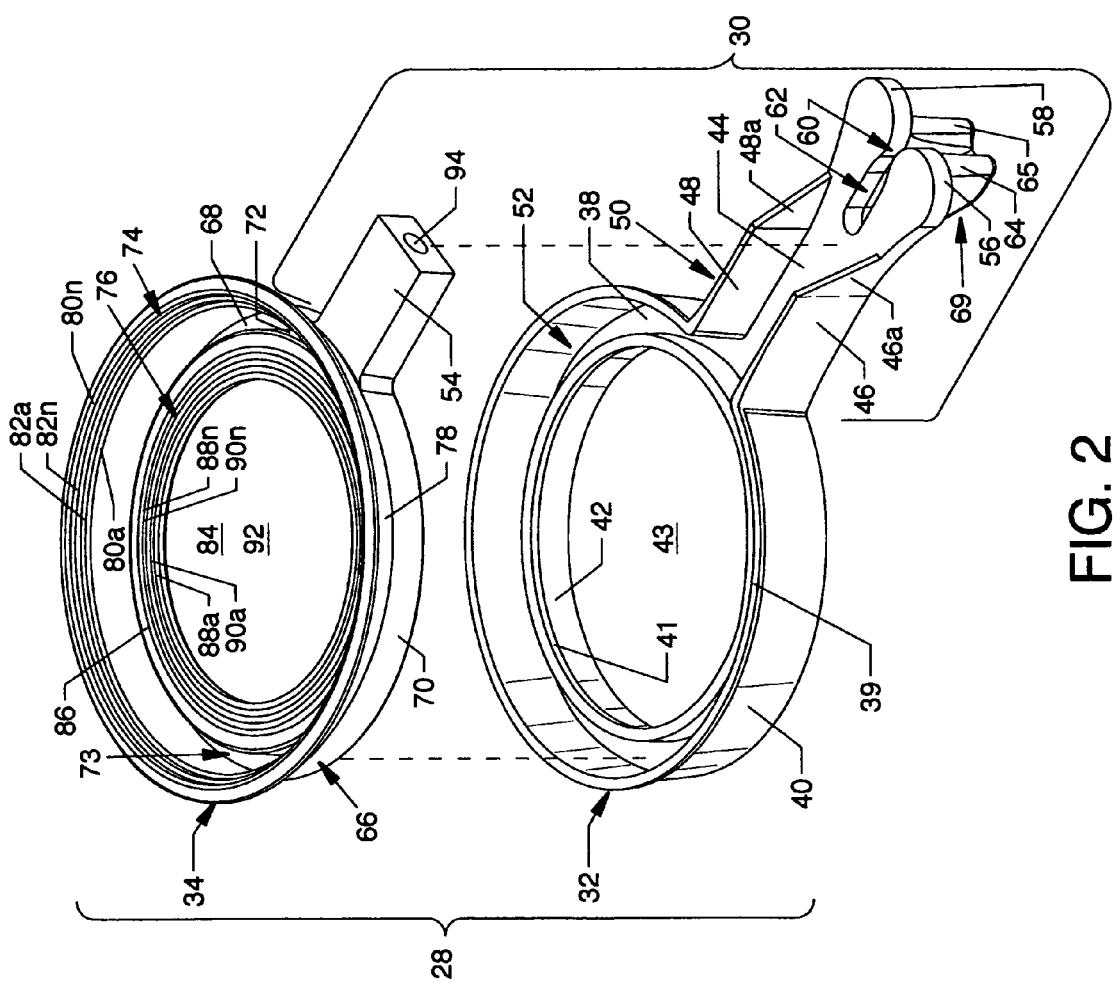
FIG. 2 is an inverted and exploded isometric view of an annular vacuum ring in a first form and an attachment fixture constituting parts of the first form of eye positioner.
Figure 3:
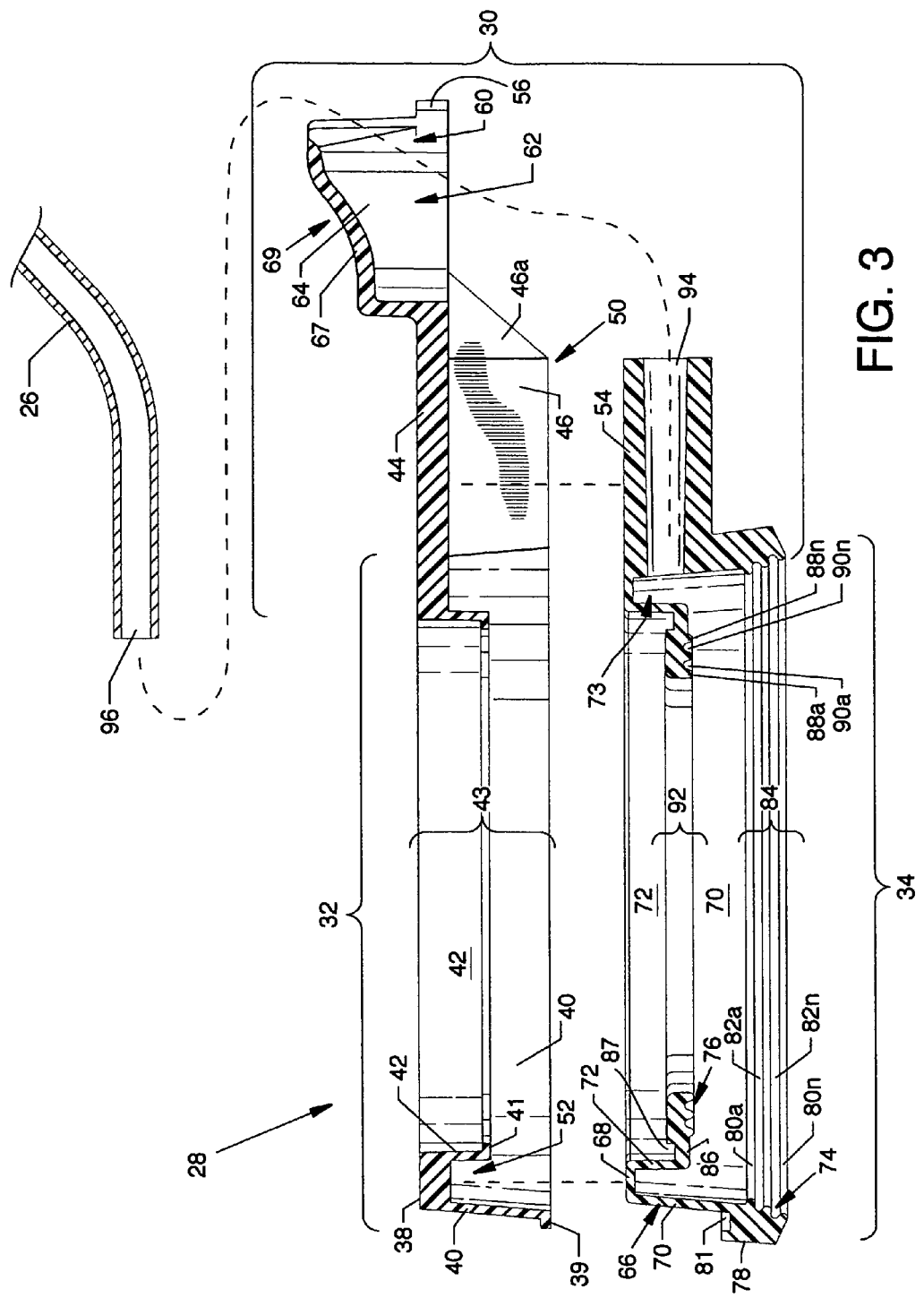
FIG. 3 is an exploded cross section side view of the first form of annular vacuum ring and the attachment fixture.

FIG. 2 is an exploded and inverted isometric view of the annular vacuum ring 28 and the components forming the attachment fixture 30, and FIG. 3 is an exploded cross section side view of the annular vacuum ring 28 and the attachment fixture 30. Preferably, the components forming one or more forms of the annular vacuum ring 28 are circular and ring-like in form, but can be of other forms, such as, but not limited to, elliptical, oval, or other suitable geometric forms. The channeled support ring 32, preferably of polypropylene, is generally annular and includes an annular panel 38 having planar features, an outer circumferential arcuate panel 40 extending from the annular panel 38, an arcuate lip 39 extending outwardly from and being the termination of the outer circumferential arcuate panel 40, a full circle inner circumferential panel 42 extending from the annular panel 38 spaced from the outer circumferential arcuate panel 40, and an annular lip 41 extending inwardly from and being the termination of the inner circumferential panel 42. A centrally located annular open space 43 extends along and about the axis of the region delineated by the inner circumferential panel 42 and the annular lip 41 in combination with and along and about the axis of the outer circumferential arcuate panel 40 and arcuate lip 39.

One part of the attachment fixture 30 includes an outwardly located section of the annular panel 38, designated generally as the planar panel extension 44, extending generally from the main body of the channeled support ring 32, as well as other geometrically configured panels or features being located on or extending from or extending through the planar panel extension 44. Opposed panels 46 and 48 having extended continuous arcuate panel ends 46a and 48a, respectively, extend perpendicularly from a greater portion of opposed edges of the planar panel extension 44. An open ended receptacle 50, which perpendicularly intersects an annular channel 52 formed by the annular panel 38, the outer circumferential arcuate panel 40, and the inner circumferential panel 42, is constituted by the opposed panels 46 and 48 and the section of the planar panel extension 44 located therebetween, for the purpose of accommodation, such as by overmolding or other suitable methods, of a housing 54 extending from the flexible sealing ring 34. The ends of the outer circumferential arcuate panel 40 and the arcuate lip 39 intersect and are continuous with one end of each of the opposed panels 46 and 48, respectively. Additional structure and features are included at or in close proximity to the outboard end of the planar panel extension 44 which, in close association with the receptacle 50 and the housing 54, facilitate and complement the fastening of the rigid hollow tube 26 to the annular vacuum ring 28. Such additional structure and features include the outboard end of the planar panel extension 44 incorporating a flexible feature including outwardly facing opposed arcuate sections 56 and 58 and other features now described. An engagement channel 62 is continuous with a connecting narrower restrictive access channel 60 both formed by opposed stabilizer panels 64 and 65 extending from the opposed arcuate sections 56 and 58 and being flexibly associated to allow forcible accommodation of the rigid hollow tube 26 therebetween. The opposed stabilizer panels 64 and 65 are continuously formed by the inclusion of a top panel 67, thereby forming a receptor enclosure 69 that is open between the stabilizer panels 64 and 65 and the top panel 67.

The flexible sealing ring 34 includes geometrically configured structure overmolded to, along and about the accommodating annular channel 52 and the arcuate lip 39 and the annular lip 41 of the channeled support ring 32, and also includes geometrically configured structure which is sealingly accommodated by the human eye. The flexible sealing ring 34, preferably of C-flex or other like flexible material embracing overmolding, such as rubber, plastic, or the like, is overmolded onto the channeled support ring 32 and includes the housing 54 extending from the edge of the flexible sealing ring 34 and an annular connecting seal 66, the shape of which and the purpose of which is to accommodatingly and frictionally engage and seal with the annular channel 52 of the channeled support ring 32. The annular connecting seal 66 includes an annular panel 68, an outer circumferential side 70 extending from the annular panel 68, and an inner circumferential side 72 extending from the annular panel 68 and spaced from the outer circumferential side 70. The exterior portion of the annular connecting seal 66 sealingly mates by overmolding with the annular channel 52 of the channeled support ring 32. The interior portion of the annular connecting seal 66 delineates an interior annular vacuum channel 73.

Also co-located with the flexible sealing ring 34 are annular outer and inner flexible sealing arrays 74 and 76, respectively, which are incorporated to seal against the human eye. The annular outer flexible sealing ring array 74 and the annular inner flexible sealing array 76 are at differently staged levels and located in two planes, thus allowing for engagement of the eye 100 at suitable levels conducive to proper sealing to the eye 100. The annular outer flexible sealing array 74 extends along the interior region of an outwardly angled side portion 78 which extends from the outer circumferential side 70. An outer annular channel 81 is included where the outwardly angled side portion 78 joins the outer circumferential side 70. A plurality of inwardly facing and concentric eye contact rings 80$a$-80$n$ having progressively larger radii alternate with and are separated by a plurality of progressively larger radii concentric grooves 82$a$-82$n$, all of which are located at and are part of the outwardly angled side portion 78 of the flexible sealing ring 34. A centrally located annular open space 84 extends along and about the axis of the region delineated by the eye contact rings 80$a$-80$n$ and the grooves 82$a$-82$n$. The inner flexible sealing array 76 is generally of lesser overall dimension with respect to the outer flexible sealing array 74, but is of closely related structure and extends from and is disposed in horizontal fashion in the central region of the inner circumferential side 72 by incorporation of an annular panel 86. An inner annular channel 87 is located where the inner circumferential side 72 joins the annular panel 86. A plurality of downwardly facing and concentric eye contact rings 88$a$-88$n$ located on one side of the annular panel 86 and having progressively larger radii alternate with and are separated by a plurality of progressively larger radii concentric grooves 90$a$-90$n$, all of which are located central to the flexible sealing ring 34. A centrally located annular open space 92 extends along and about the axis of the region delineated by the inner circumference of the annular panel 86 where the eye contact rings 88$a$-88$n$ and the grooves 90$a$-90$n$ are located. The housing 54 is continuously molded with the flexible sealing ring 34 and extends therefrom to mate as part of the overmolding process with the receptacle 50 of the channeled support ring 32 to form a greater portion of the attachment fixture 30. The housing 54 includes a tapered bore 94 extending along the length thereof which communicates with the annular vacuum channel 73 of the flexible sealing ring 34.

Figure 4:
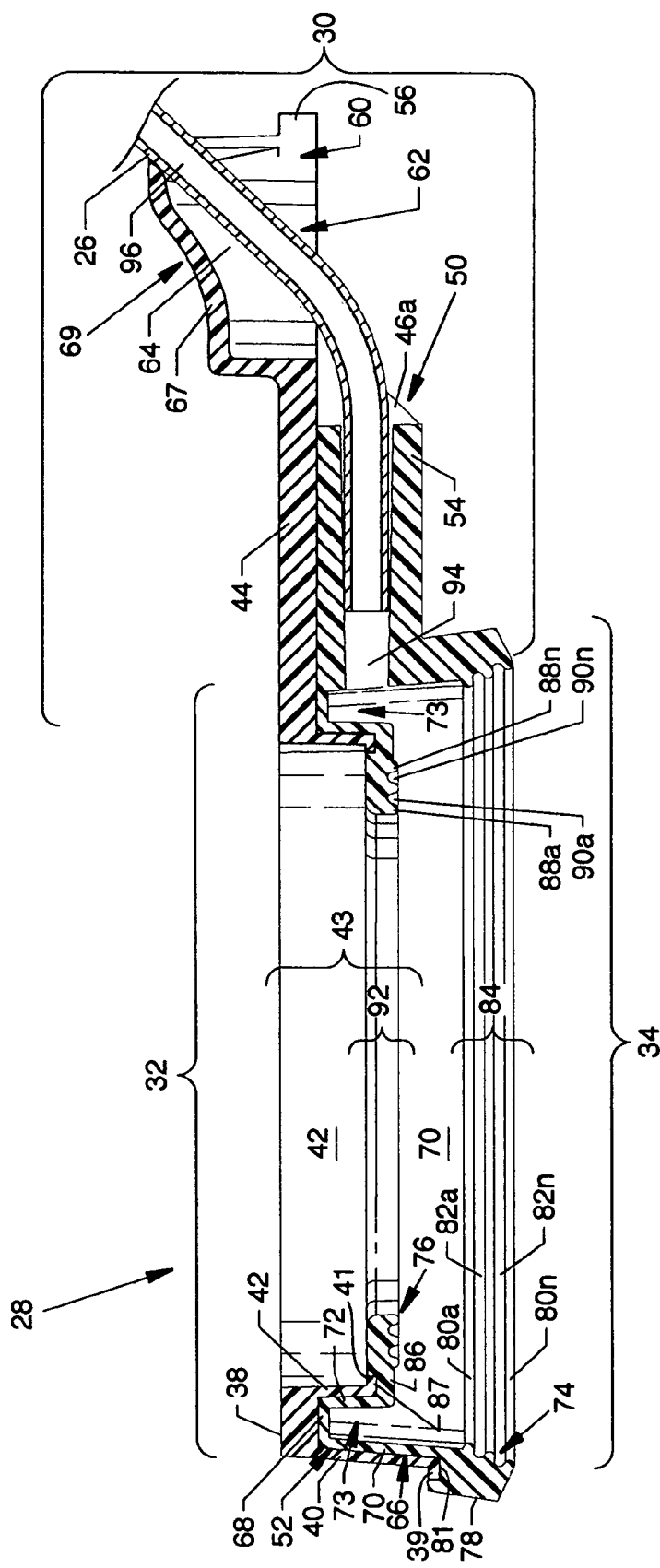
FIG. 4 is an assembled cross section view of the first form of annular vacuum ring showing the mutual engagement and accommodational overmolded relationship of the annular connecting seal of the flexible sealing ring to the annular channel of the channeled support ring.

FIG. 4 is an assembled cross section view of the annular vacuum ring 28 previously shown and described showing the mutual engagement and accommodational overmolded relationship of the annular connecting seal 66 of the flexible sealing ring 34 to the annular channel 52 of the channeled support ring 32. The channeled support ring 32 provides support for the overmolded flexible sealing ring 34. Also shown is the relationship of the lumen 96 of the rigid hollow tube 26 which communicates with the annular vacuum channel 73 of the flexible sealing ring 34. Housing 54, which is closely associated with the flexible sealing ring 34, is shown in intimate contact and accommodation by the receptacle 50 which is closely associated with the channeled support ring 32. The distal end of the rigid hollow tube 26 forcibly engages the taper of the tapered bore 94 to promote a complete and sound connection to and within the tapered bore 94 in concert with attachment features to suitably and sealingly communicate with the tapered bore 94 and thus to promote complete and sound communication between the lumen 96 of the rigid hollow tube 26 and the annular vacuum channel 73 of the flexible sealing ring 34, whereby communication is also provided with the syringe 14 and associated relevant components. Also shown is the overmolding association of the inner annular channel 87 which is overmolded to the annular lip 41 and the outer annular channel 81 which is overmolded to the arcuate lip 39.

Figure 5:
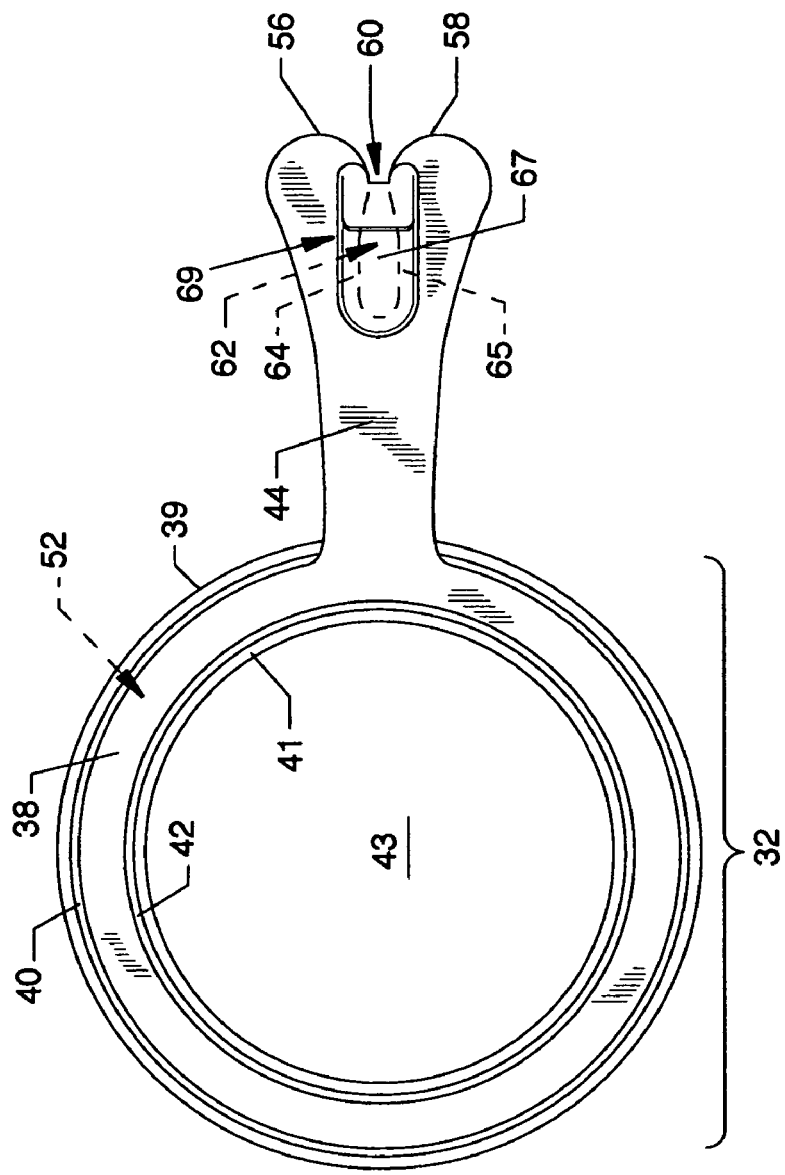
FIG. 5 is a top view of the channeled support ring.

FIG. 5 is a top view of the channeled support ring 32. Especially shown is the receptor enclosure 69 extending outwardly from the planar panel extension 44 in a direction away from the annular channel 52. The structure of the restrictive access channel 60 and engagement channel 62 of the continuously formed receptor enclosure 69 is flexible across the centerline of the planar panel extension 44 in order to flexibly accept and snappingly engage the diameter of the rigid hollow tube 26. During installation of the rigid hollow tube 26 within the engagement channel 62, the rigid hollow tube 26 can first forcibly engage the arcuate sections 56 and 58 and then the restrictive access channel 60 to cause flexing of the arcuate sections 56 and 58 across the centerline of the planar panel extension 44, thereby allowing passage of the sides of the rigid hollow tube 26 to subsequently enter the openly flexed engagement channel 62, whereupon the structure of the restrictive access channel 60 and engagement channel 62 and adjoining continuously formed stabilizer panels 64 and 65 relax to the former shape to cause forcible snap engagement about the rigid hollow tube 26. The stabilizer panels 64 and 65 offer lateral support for stabilization of the rigid hollow tube 26 along a greater portion of the rigid hollow tube 26, as later shown and discussed in detail.

Figure 6:
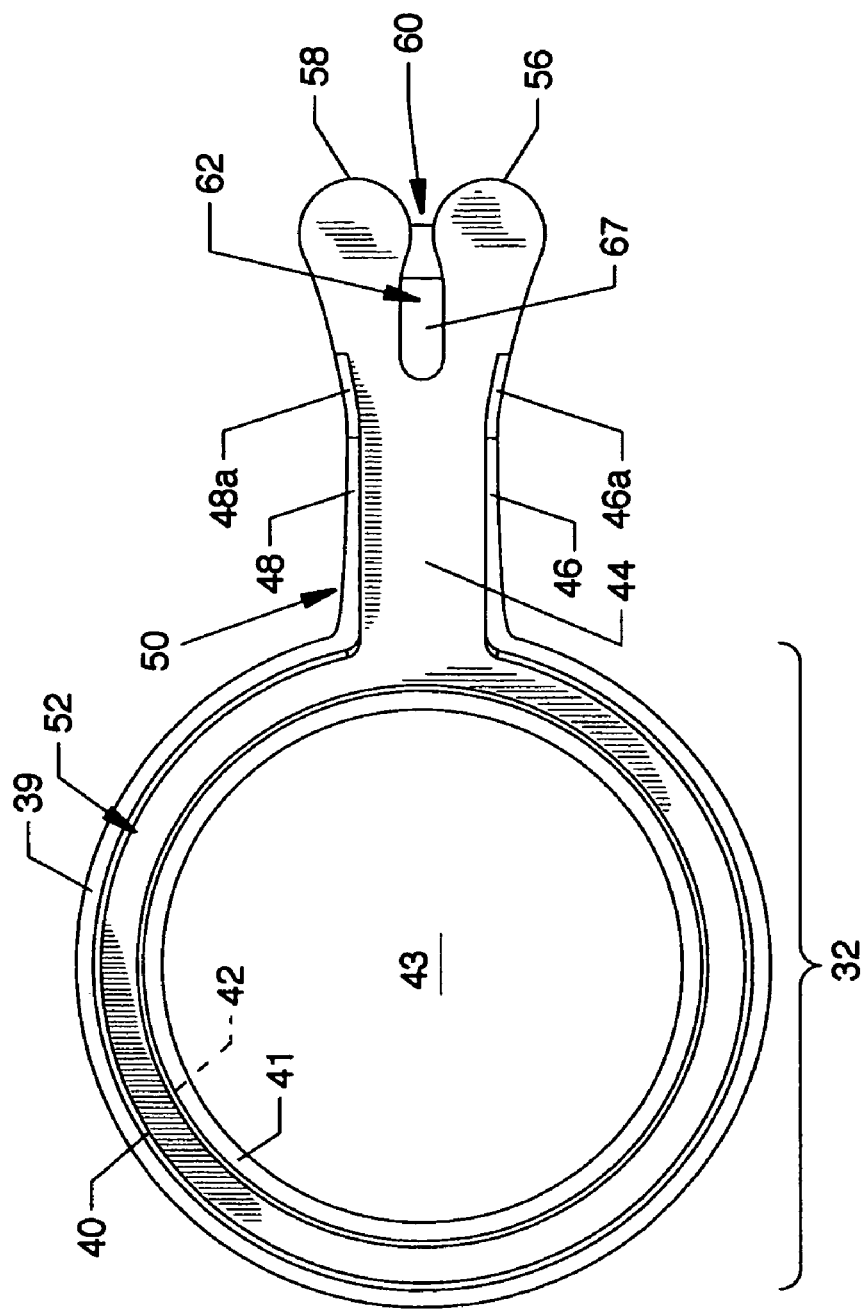
FIG. 6 is a bottom view of the channeled support ring.

FIG. 6 is a bottom view of the channeled support ring 32. Especially shown is the receptacle 50 extending outwardly from the planar panel extension 44 in a direction away from the stabilizer panels 64 and 65.

Figure 7:
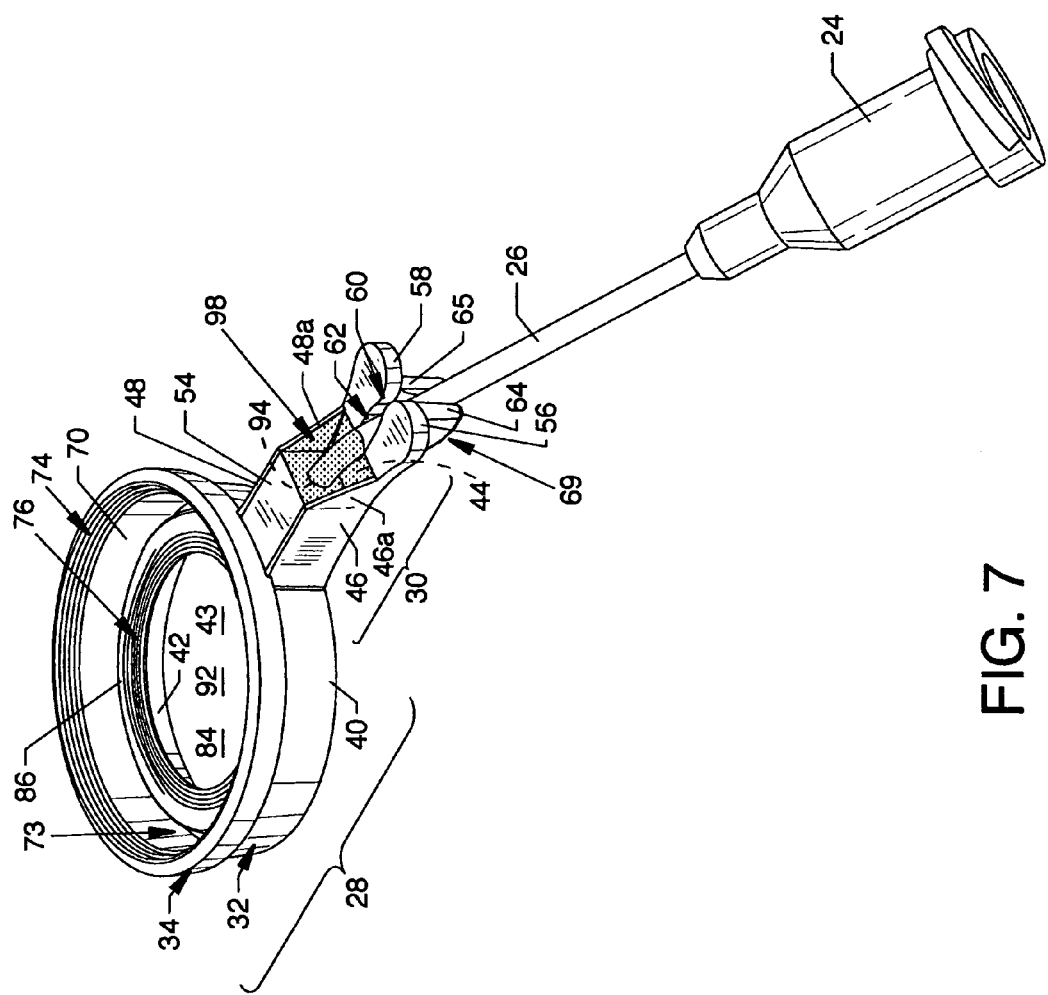
FIG. 7 is an inverted isometric view of the rigid hollow tube in firm and permanent secure engagement with the attachment fixture.
Figure 10:
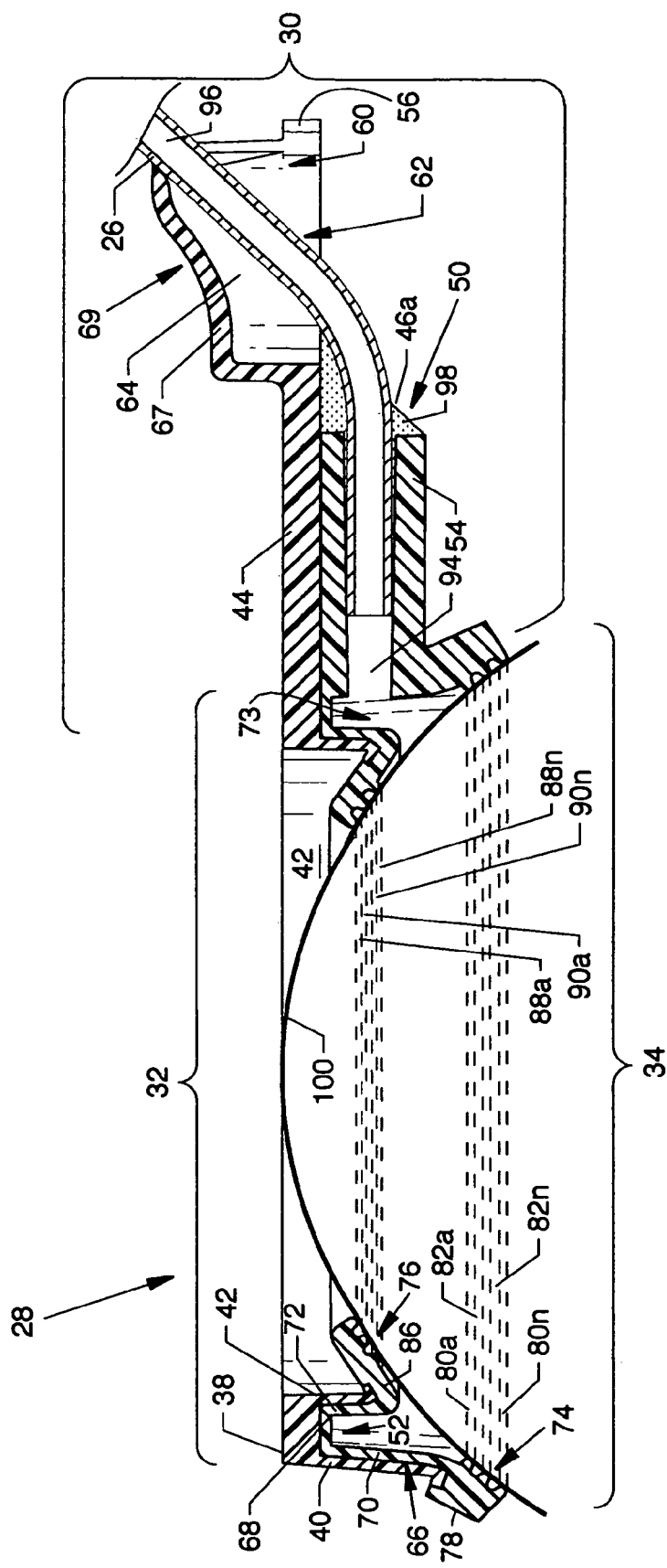
FIG. 10 illustrates the mode of operation of the first form of eye positioner.

FIG. 7 is an inverted isometric view of the rigid hollow tube 26 in firm and permanent secure engagement with the attachment fixture 30 including the housing 54, thereby causing and ensuring firm and permanent secure engagement of the rigid hollow tube 26 to the annular vacuum ring 28. Such firm and permanent secure engagement is initiated as first described in detail with reference to FIG. 5 where, in addition and in simultaneous or near simultaneous action, the distal portion of the rigid hollow tube 26 is made to forcibly and connectingly engage the taper of the tapered bore 94 of the housing 54. Preferably, a suitable adhesive 98, such as, but not limited to, silicone adhesive, is incorporated, as shown, to seal around and about a suitable distal portion of the rigid hollow tube 26, whereby the adhesive 98, in addition to application around and about the suitable distal portion of the rigid hollow tube 26, is also applied to and between the arcuate panel ends 46a and 48a, along and about the portion of the planar panel extension 44 extending between the arcuate panel ends 46a and 48a, along and about the end of the housing 54 located at the tapered bore 94, and may extend along the space between the distal portion of the rigid hollow tube 26 and the taper of the tapered bore 94, as shown in FIG. 10.

Figure 8:
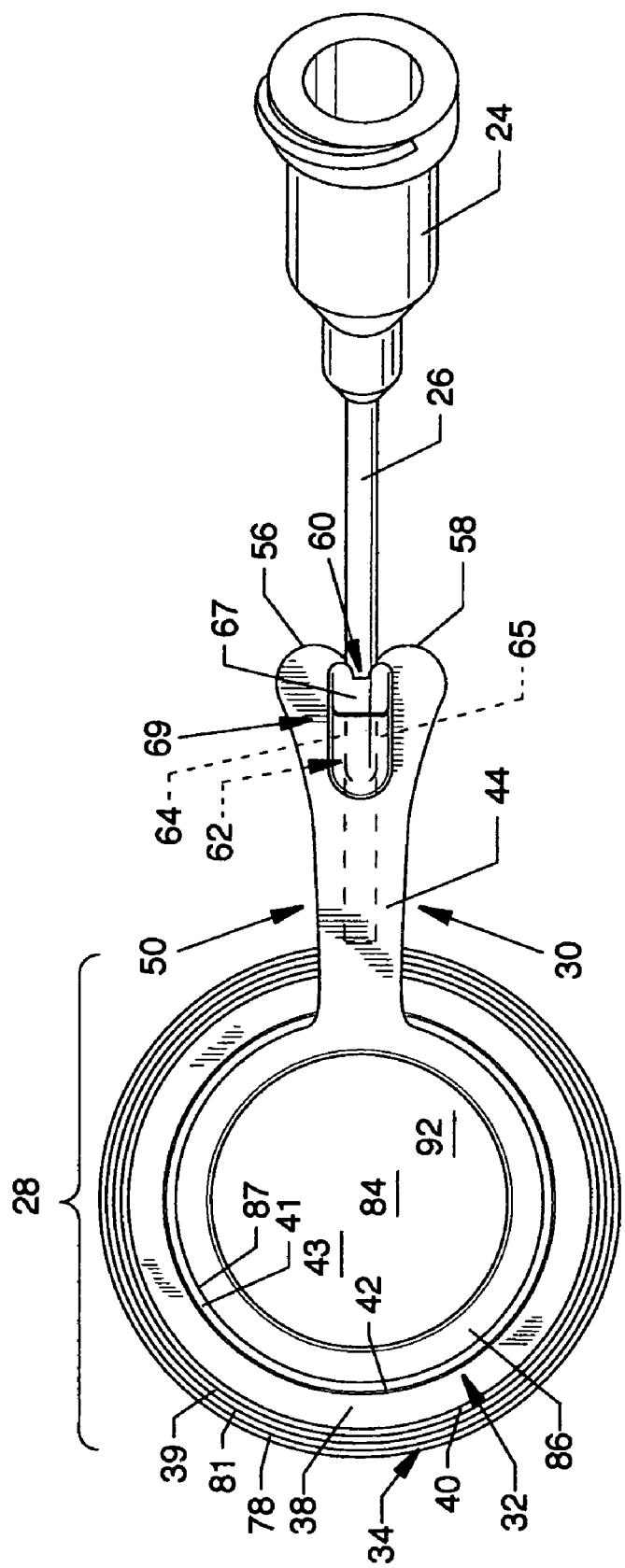
FIG. 8 is a top view of the first form of annular vacuum ring showing attachment of the rigid hollow tube and the Luer thereto using the attachment fixture.

FIG. 8 is a top view of the annular vacuum ring 28 showing attachment of the rigid hollow tube 26 and the Luer adapter 24 thereto using the attachment fixture 30.

Figure 9:
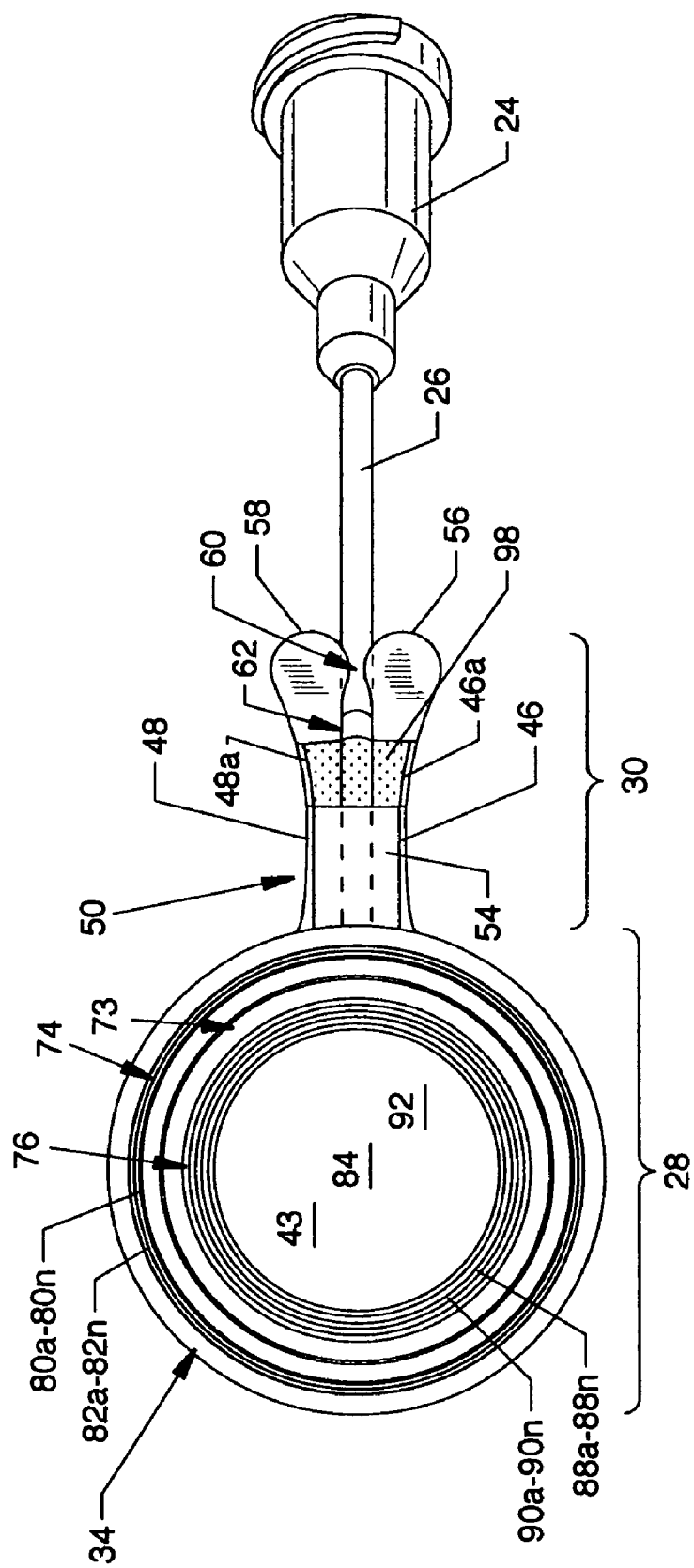
FIG. 9 is a bottom view of the first form of annular vacuum ring showing attachment of the rigid hollow tube and the Luer adapter thereto using the attachment fixture.

FIG. 9 is a bottom view of the annular vacuum ring 28 showing attachment of the rigid hollow tube 26 and the Luer adapter 24 thereto using the attachment fixture 30.

MODE OF OPERATION

FIG. 10 illustrates the mode of operation of the first form of eye positioner 10. The annular vacuum ring 28 is aligned in gentle contact to engage the eye 100 just outside the limbus. The annular vacuum ring 28 is positioned manually to cause the outer flexible sealing array 74 and the inner flexible sealing array 76 to flex about the outer circumferential side 70 and the inner circumferential side 72, respectively, whereby the outer flexible sealing array 74 and the inner flexible sealing array 76 flexibly align to the contour of the eye 100. Subsequent to suitable engagement, the syringe plunger shaft 16 is suitably actuated outwardly to cause sufficient vacuum to be created between the members of the flexible sealing ring 34 and the arcuate area of the eye 100 encompassed by the eye contact rings 80a-80n of the outer flexible sealing array 74 and the eye contact rings 88a-88n of the inner flexible sealing array 76. Such action allows the eye 100 to be grasped, maneuvered and suitably positioned for surgical or other techniques. Spring 18 assists the outward movement of the syringe plunger shaft 16.

The syringe 14 and flexible sealing ring 34 can be manufactured from a variety of suitable materials, such as metal or plastic or any other suitable material. Different capacity syringes 14 can be used to change vacuum level. Additional flexible sealing rings of various diameters can be utilized. The vacuum producing means in the instrument handle can be any mechanical pump, such as the described syringe, or can be a hand pump. Alternative vacuum producing devices can be powered by electricity, such as battery or other electric supplies. The annular vacuum ring 28 can be a complete circle or have a feature for accessibility of instruments.

Additionally, as previously described, a plurality of accompanying closely associated auxiliary devices are provided for use with the eye positioner 10, some of which include but which are not limited to flexible tubing, stopcocks and Luer connection devices which can be utilized in various combinations to enhance the operation of the eye positioner 10 and to provide for multiple uses and configurations involving the use of the eye positioner 10.

Figure 11:
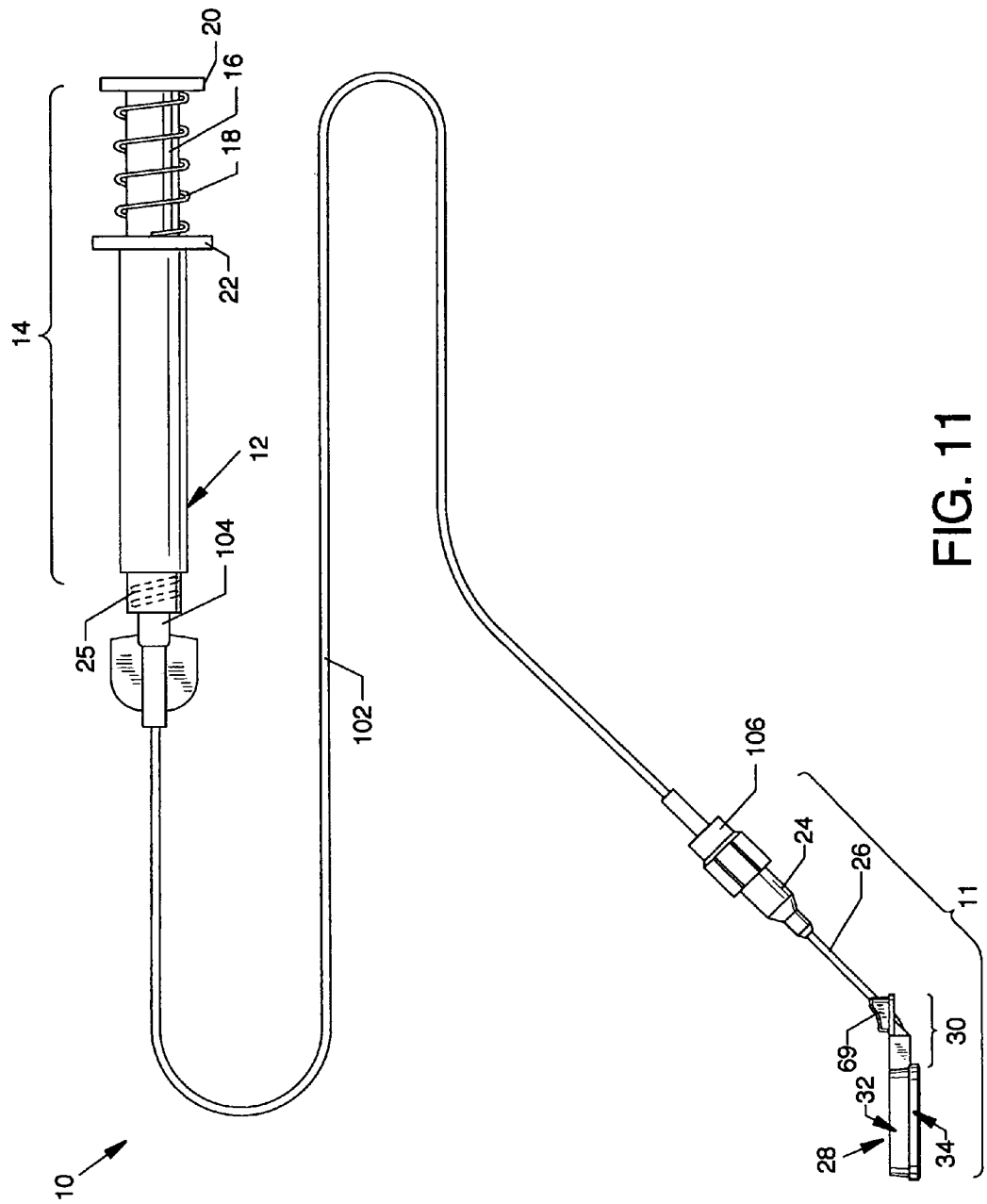
FIG. 11 shows the flexible coupling of and the distancing of the syringe from the general structure of the eye positioner by the use of a flexible tube.

FIG. 11 is an example closely related to much of the structure of and which employs many of the benefits described in previous figures. FIG. 11 shows the flexible coupling of and the distancing of the syringe 14 from the other components of the previously described eye positioner 10 constituting a general structure 11 where it is considered advantageous to have the structure and bulk of the syringe 14 removed from rigid contact with the general structure 11 including, but not limited to, the Luer adapter 24, the rigid hollow tube 26, the attachment fixture 30 and the components forming the annular vacuum ring 28. Removal of the syringe 14 from direct contact with the general structure 11 provides several advantages some of which are the following: minimizing off center tipping of the general structure 11 which can be caused by the weight of the combined syringe 14 and general structure 11 when attached to an eye; removal of the syringe 14 from the near vicinity surrounding the medical procedure, thereby providing a less cluttered medical procedure site; and distant operation of the syringe 14 when it is desirable to maintain stability of the general structure 11 with respect to the eye. Distancing of the syringe 14 from the general structure 11 incorporates the use of a plastic or otherwise suitably constructed flexible tube 102 having Luer connectors 104 and 106 attached at opposite ends. Luer connector 104 connects one end of the flexible tube 102 to the internally threaded end 25 of the syringe 14, and Luer connector 106 connects the other end of the flexible tube 102 to the Luer adapter 24, and thus to the general structure 11 for operation thereof. The physician can utilize the combined structure of the rigid hollow tube 26, the Luer adapter 24, and the Luer connector 106 as a handle for maneuvering of the annular vacuum ring 28 and the eye coupled thereto.

Figure 12:
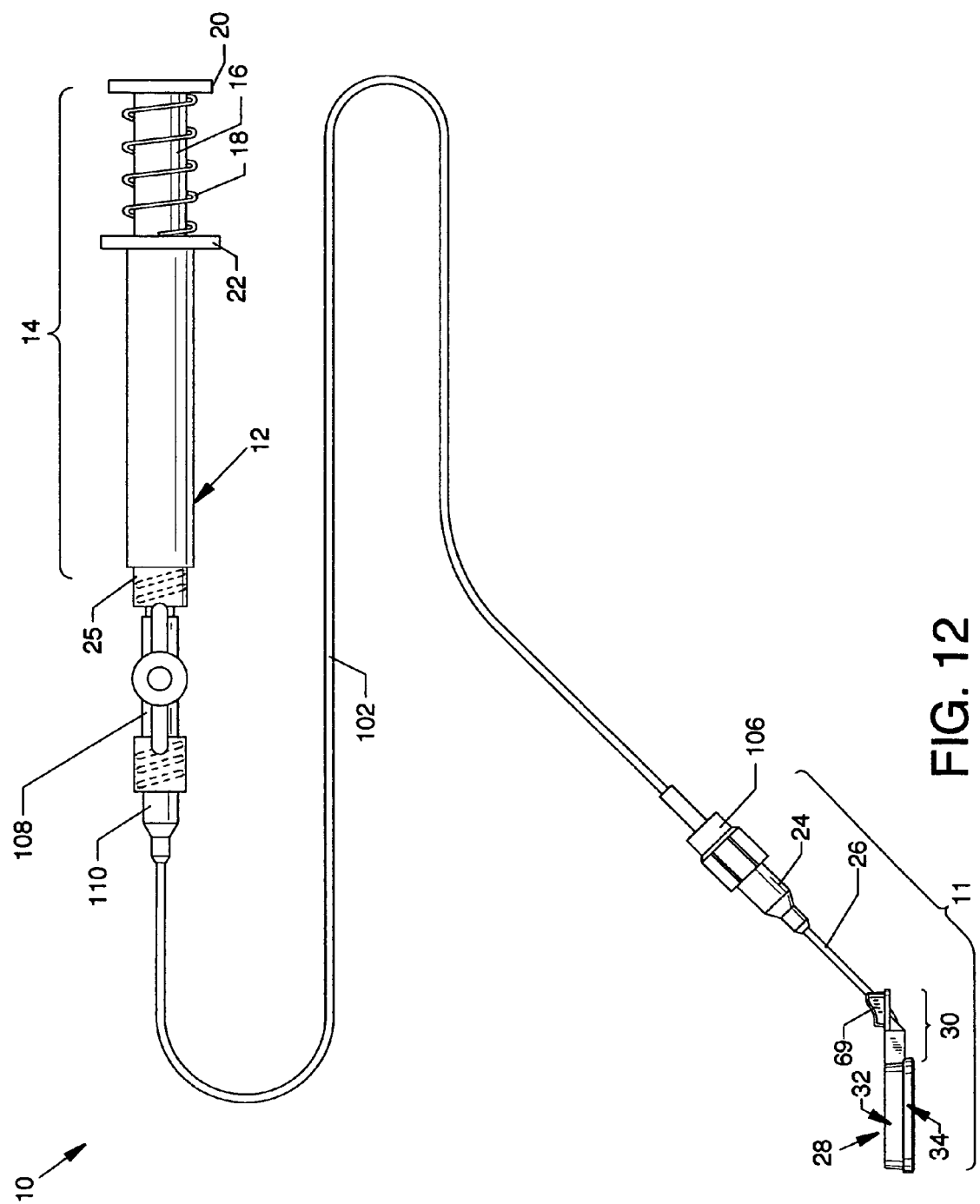
FIG. 12 shows the flexible coupling of and the distancing of the syringe from the general structure of the eye positioner by the use of a flexible tube and a stopcock located adjacent to the syringe.

FIG. 12 is an example closely related to much of the structure of and which employs many of the benefits described in previous figures, including FIG. 11, showing the flexible coupling of and the distancing of the syringe 14 from the other components of the eye positioner 10 constituting the general structure 11 where it is considered advantageous to have the structure and bulk of the syringe 14 removed from rigid contact with the general structure 11. A stopcock 108 and a Luer adapter 110 are included in lieu of the Luer connector 104 of FIG. 11, whereby the Luer adapter 110 is attached to one end of the flexible tube 102. One end of the stopcock 108 connects to the internally threaded end 25 of the syringe 14. The Luer adapter 110 connects to the other end of the stopcock 108 and, as previously described, the Luer connector 106 connects the other end of the flexible tube 102 to the Luer adapter 24, and thus to the general structure 11 for operation thereof. When a suitable vacuum for engaged coupling of the annular vacuum ring 28 to an eye is achieved by manipulation of the syringe plunger shaft 16, the stopcock 108 can be closed to maintain a stable vacuum within the annular vacuum ring 28 and within the attached flexible tube 102 without being concerned about inadvertent movement of the syringe plunger shaft 16 either by personnel or by internal slippage. Subsequently, the syringe 14 can be removed from the stopcock 108. The physician can utilize the combined structure of the rigid hollow tube 26, the Luer adapter 24, and the Luer connector 106 as a handle for maneuvering of the annular vacuum ring 28 and the eye 100 coupled thereto even though the flexible tube 102 is attached.

Figure 13:
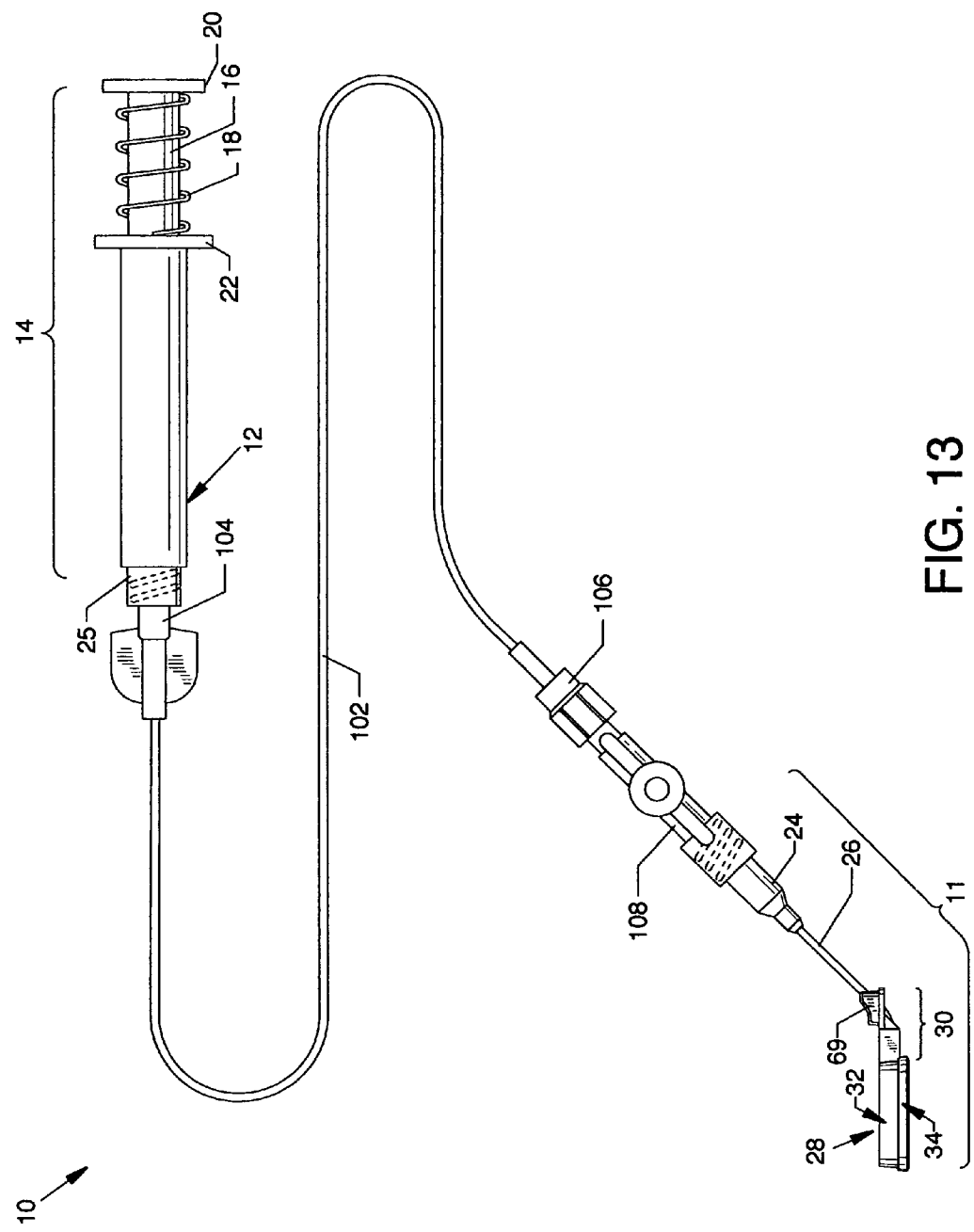
FIG. 13 shows the flexible coupling of and the distancing of the syringe from the general structure of the eye positioner by the use of a flexible tube and a stopcock positioned adjacent to the Luer adapter coupled to the rigid hollow tube.

FIG. 13 is an example closely related to much of the structure of and which employs many of the benefits, described in previous figures, including FIGS. 11 and 12, showing the flexible coupling of and the distancing of the syringe 14 from the other components of the eye positioner 10 constituting the general structure 11 where it is considered advantageous to have the structure and bulk of the syringe 14 removed from rigid contact with the general structure 11. In the alternative, as shown in this figure, the stopcock 108 is inserted between the Luer adapter 24 and the Luer connector 106 instead of at the syringe 14 and is operated much in the same manner as described in relation to FIG. 12. In this example, after the stopcock 108 is closed to maintain operating vacuum, the Luer connector 106 can be loosened and removed along with the flexible tube 102 from the stopcock 108 leaving a structure, such as shown in FIG. 15, whereby the physician can utilize the combined structure of the rigid hollow tube 26, the Luer adapter 24, and the stopcock 108 as a handle for maneuvering of the annular vacuum ring 28 and the eye 100 coupled thereto.

Figure 14:
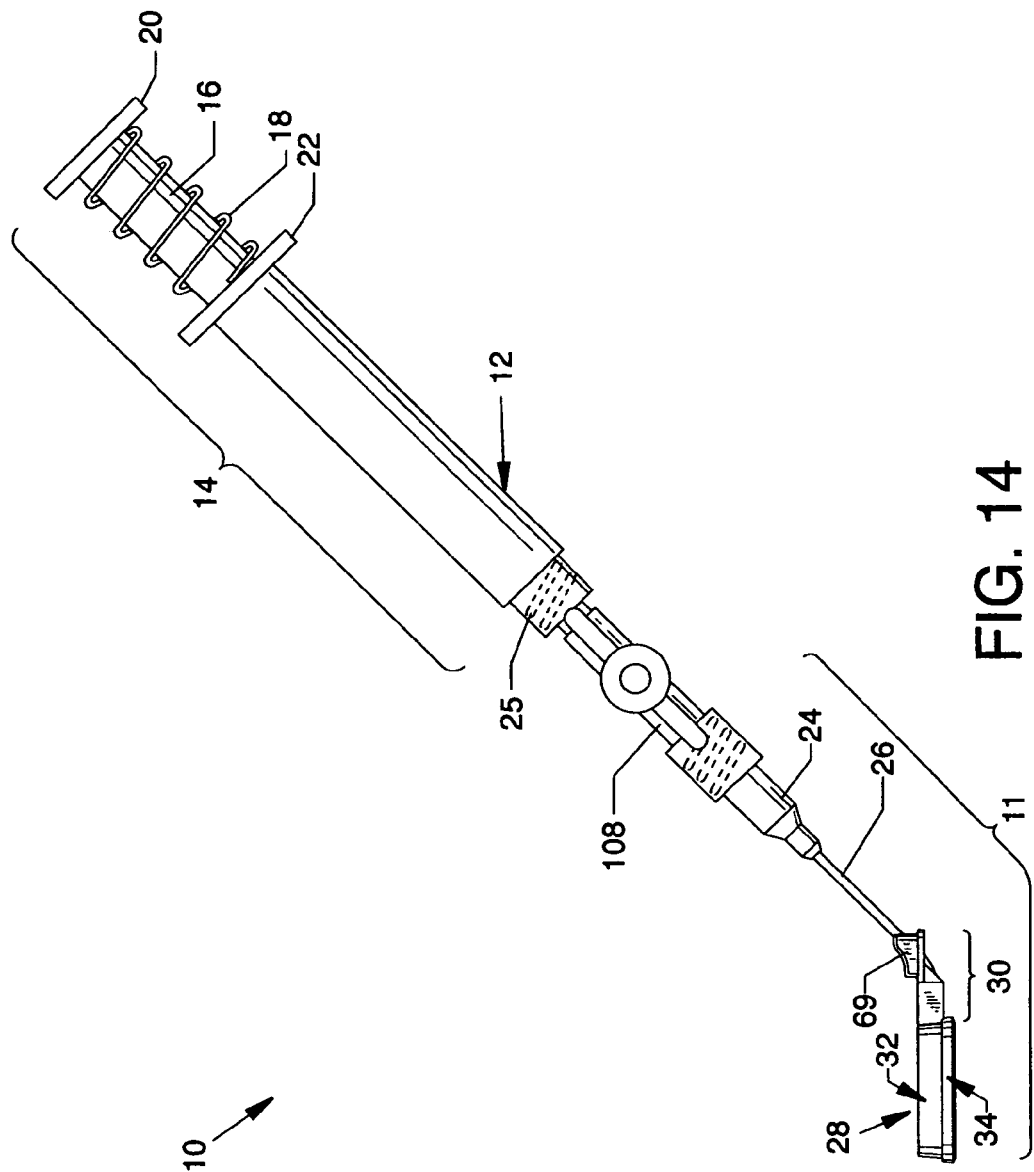
FIG. 14 shows the use of a stopcock between the general structure of the eye positioner and the syringe.

FIG. 14 is an example closely related to much of the structure of and which employs some of the benefits described in previous figures, including FIGS. 11, 12 and 13, showing the syringe 14 connected to the Luer adapter 24 of the general structure 11 by the stopcock 108 and operated much in the same manner as described in relation to FIG. 12. In this example, after the stopcock 108 is closed to maintain operating vacuum, the syringe 14 can be removed from the Luer adapter 24 leaving a structure such as shown in FIG. 15, whereby the physician can utilize the combined structure of the rigid hollow tube 26, the Luer adapter 24, and the stopcock 108 as a handle for maneuvering of the annular vacuum ring 28 and the eye 100 coupled thereto.

Figure 15:
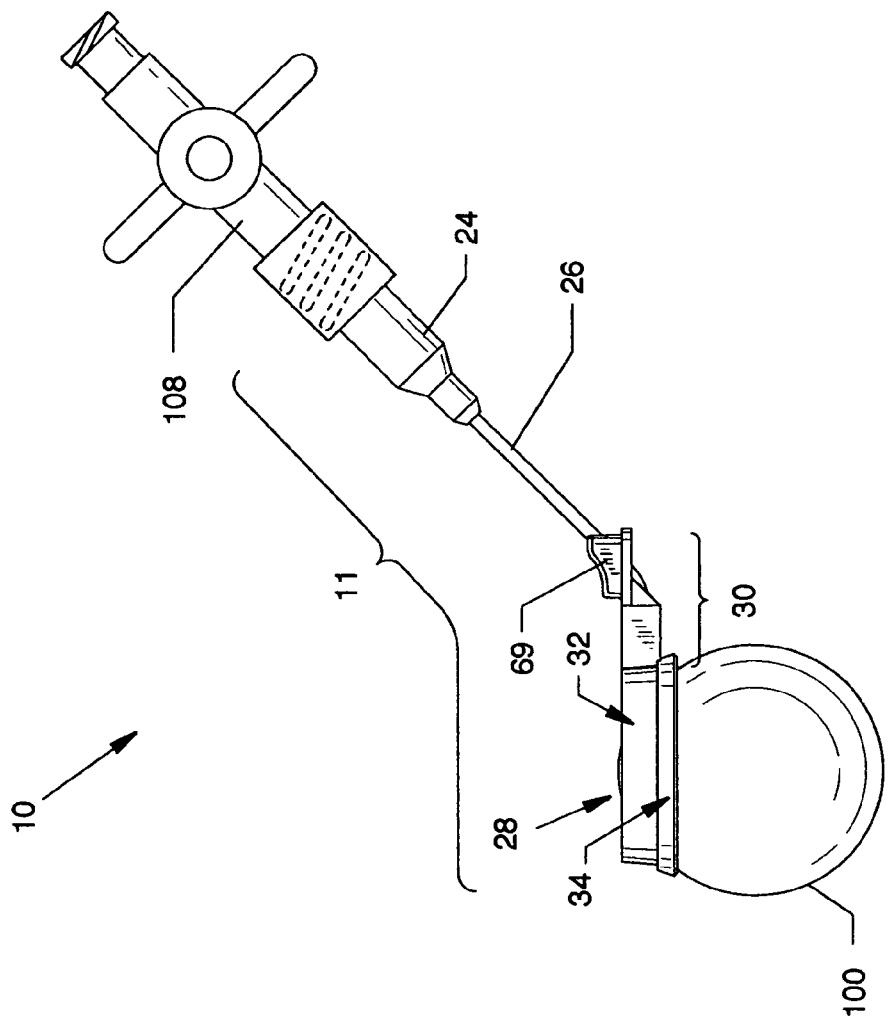
FIG. 15 shows the use of the stopcock as a handle.

FIG. 15 is an example closely related to much of the structure of and which employs some of the benefits described in previous figures, including FIGS. 11, 12, 13 and 14. The components of FIG. 15 are shown where the stopcock 108 is in a closed position, such as described for use in FIGS. 13 and 14, whereby the physician can utilize the combined structure of the rigid hollow tube 26, the Luer adapter 24, and the stopcock 108 as a handle for maneuvering of the annular vacuum ring 28 and the eye 100 coupled thereto.

Figure 16:
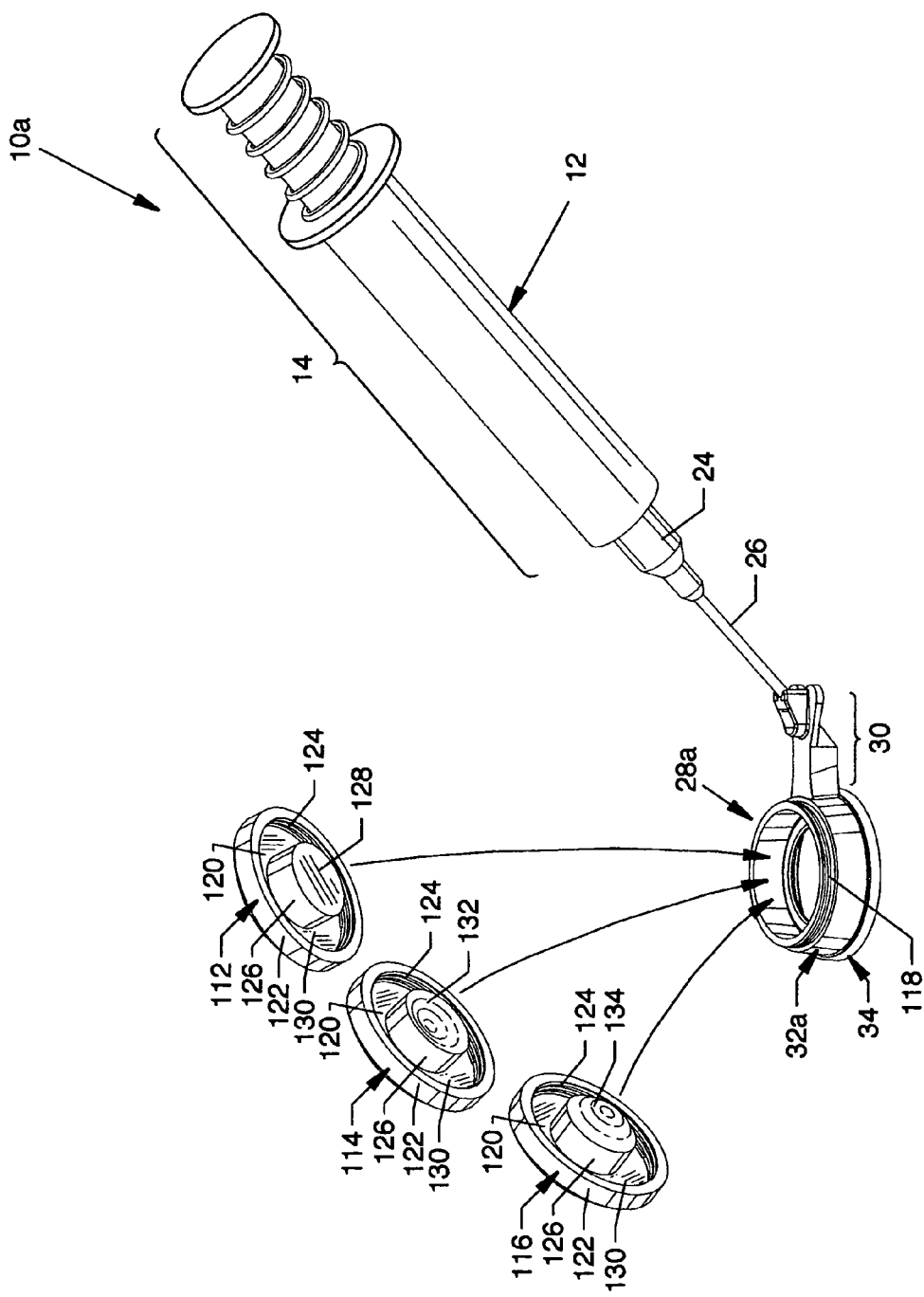
FIG. 16 is an isometric view of a second form of eye positioner for use with a variety of differently shaped lenses or closely related structures.
Figure 17:
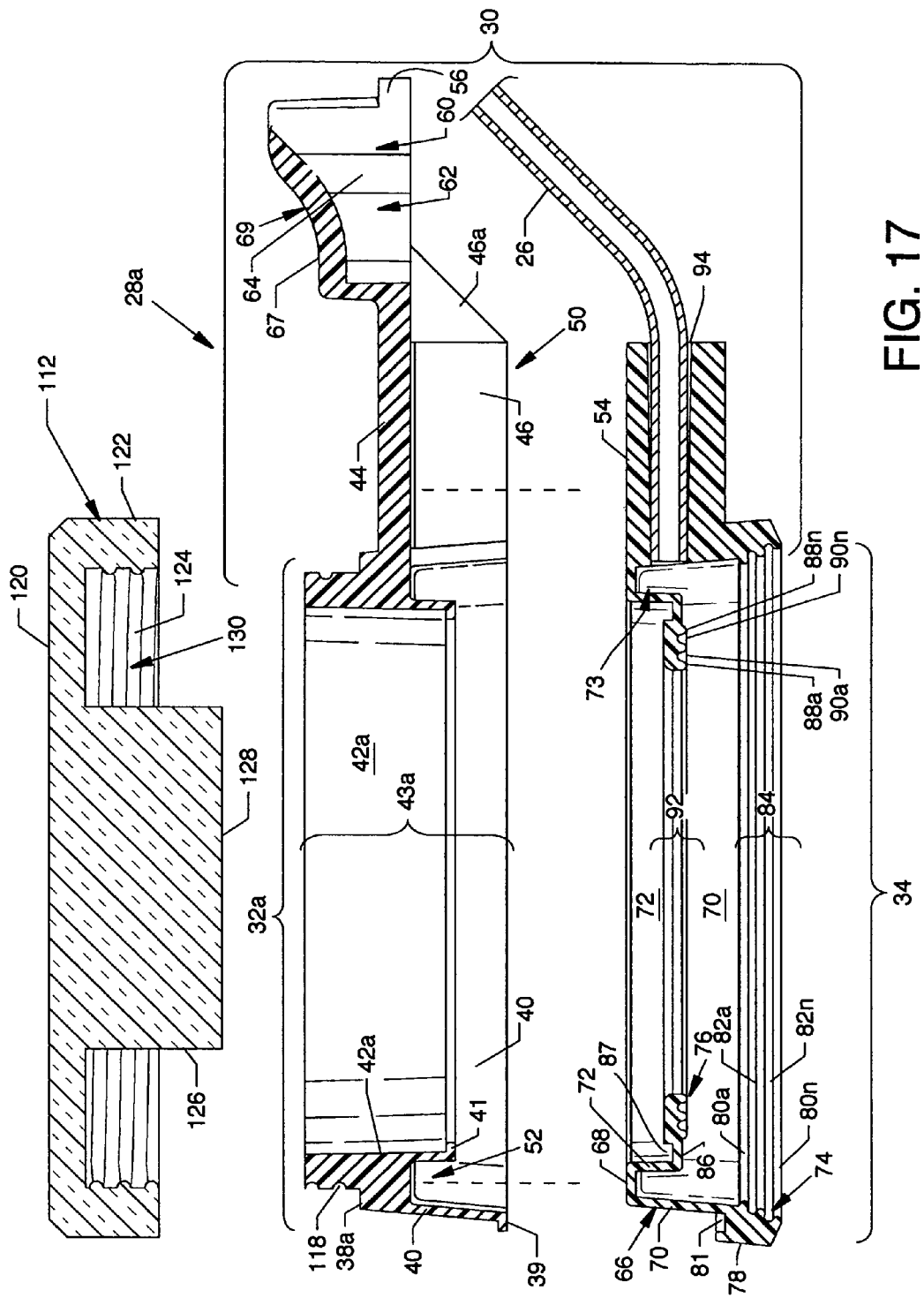
FIG. 17 is like FIG. 3 and shows an exploded cross section side view of an annular vacuum ring in a second form and of a plano-plano lens in alignment therewith.

In FIGS. 16-17, several closely related components or closely related features are redesignated owing to elongation or minor geometrical configuration and include an alphabetical suffix appended to a previously described component reference character or feature. FIG. 16 is an isometric view of a second form of eye positioner 10a for use with a variety of differently shaped or suitably configured lenses or closely related structures generally referred to as, but not limited to, a plano-plano lens 112, a plano-concave lens 114, and a plano-convex lens 116, or for use as previously described. Any suitably shaped or configured lens could be used where one style would employ a concave shape to conform to the eye or any other lens shape for transfer of light, sound or electromagnetic rays for condensing, focusing, diffusing, or blocking the rays or aiding in visualization. The plano-plano lens 112, the plano-concave lens 114, and the plano-convex lens 116, which can be inserted into the interior of the annular vacuum ring 28a, can utilize lens material which can be clear, but could also be variably clear or alternatingly clear and opaque to allow a certain effect from various energy applications. The eye positioner 10a differs from the eye positioner 10 where the annular vacuum ring 28 is redesignated as an annular vacuum ring 28a and where the channeled support ring 32 has been redesignated as a channeled support ring 32a, as well as by other features. An annular threaded fixture 118 is included at the upper portion of the annular vacuum ring 28a for one at a time accommodation of any of a plano-plano lens 112, a plano-concave lens 114, or a plano-convex lens 116, each preferably including internal threads which secure the respective lenses to the annular vacuum ring 28a, as described later in detail.

FIG. 17 is like FIG. 3 and shows an exploded cross section side view of the annular vacuum ring 28a and of the plano-plano lens 112 in alignment therewith. The annular threaded fixture 118 is included at the upper portion of the channeled support ring 32a extending from a raised annular panel 38a. Correspondingly, the vertical dimension of the inner circumferential panel 42a and the annular open space 43a is increased slightly with respect to the previously shown inner circumferential panel 42 and annular open space 43. The one-piece annular plano-plano lens 112 includes a planar top 120, a circumferential side 122 extending from the periphery of the planar top 120, threads 124 on the inner portion of the circumferential side 122, a round extension 126 extending beyond the circumferential side 122 from the underside of the planar top 120 terminated by a planar surface 128, and an annular space 130 between the threads 124, the planar top 120 and the extension 126. The plano-concave lens 114 and a plano-convex lens 116, shown in FIG. 16, are similarly configured but differ by the inclusion of a concave surface 132 or a convex surface 134 in lieu of the planar surface 128 to constitute the plano-concave lens 114 or the plano-convex lens 116, as shown in FIG. 16. Although plano, concave and convex surfaces for shaping the eye 100 are described, other geometrically configured shapes can be incorporated into the end of the extensions 126 to provide for a variety of different shaping surfaces.

Figure 18:
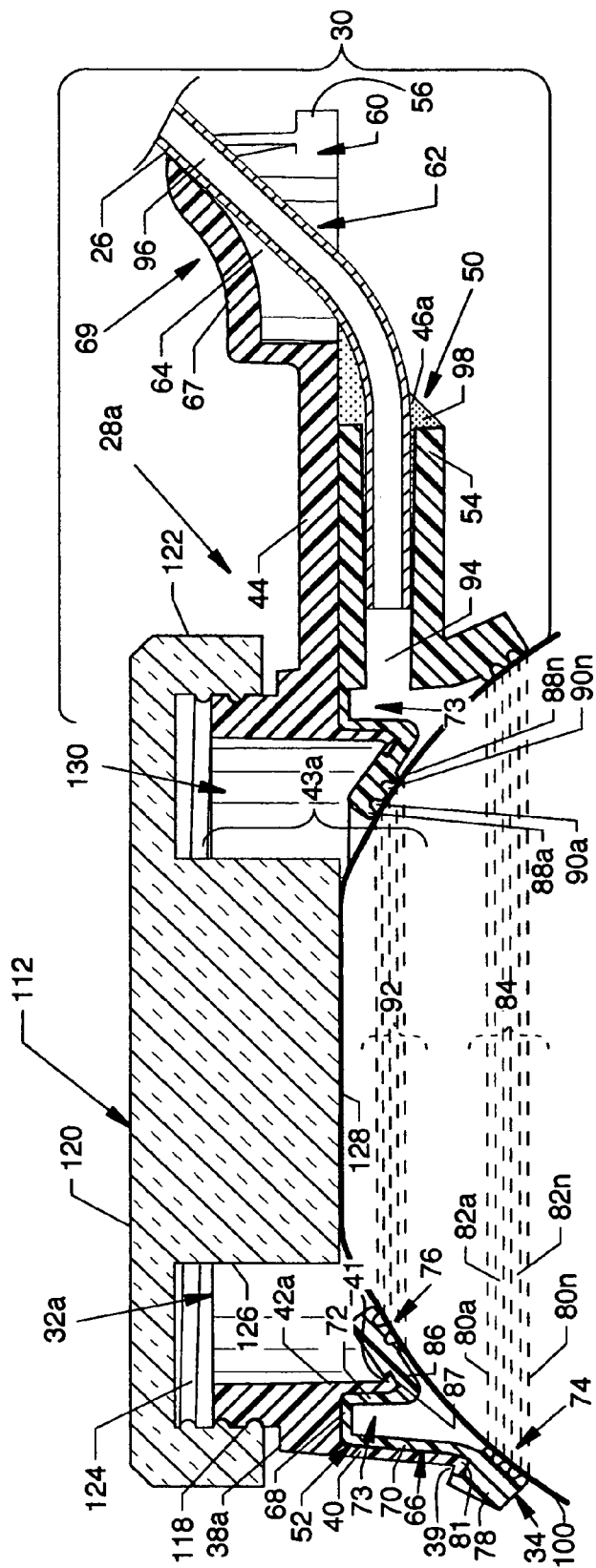
FIG. 18 is an assembled cross section view of the second form of annular vacuum ring illustrating the second form of annular vacuum ring aligned with and in gentle contact and engagement with the eye.

FIG. 18 is an assembled cross section view of the annular vacuum ring 28a illustrating the annular vacuum ring 28a aligned with and in gentle contact and engagement with the eye 100 just outside the limbus, such as shown in FIG. 10, and of the plano-plano lens 112 in shape altering contact with the eye 100. The threads 124 of the plano-plano lens 112 are shown is mutual engagement with the threads of the threaded fixture 118 of the channeled support ring 32a, thereby adjustably securing the plano-plano lens 112 to the threaded fixture 118 of the channeled support ring 32a, and thus to the annular vacuum ring 28a. The round extension 126 including the planar surface 128 extends into a portion of the annular open space 43a of the annular vacuum ring 28a and in this case the eye 100 is gently but forcibly reshaped by intimate contact with the planar surface 128 of the plano-plano lens 112 to assume a flat and planar contact region. Alternatively, concave or convex reshaping of the eye 100 can be effected by use of the plano-concave lens 114 having the concave surface 132 or by the use of the plano-convex lens 116 having the convex surface 134, respectively. Once reshaping to the desired shape or form has been accomplished, procedures, such as with visible light application to the lens of the eye or a pseudophakos, or to the retina, such as in argon or diode laser application, or to the cornea, such as, but not limited to, excimer laser or femtosecond laser application, any other procedure can be performed. Also, once the laser or other energy has been applied, any other procedure, such as repositioning ocular tissue, incisional surgery, or suturing, can be performed. The use of threads 124 in engagement with the threaded fixture 118 has been described herein to attach either the plano-plano lens 112, the plano-concave lens 114, or the plano-convex lens 116 to the annular vacuum ring 28a. In the alternative, other suitable arrangements for removable attachment of the lenses to the annular vacuum ring 28a can be employed, such as, but not limited to, ring and groove arrangements, rotatable locked arrangements incorporating bayonet and grooves, such as used in light bulb-to-socket engagement, slotted flexible members of the lenses which can engage the inner circumferential panel 42a, and the like.

Figure 19:
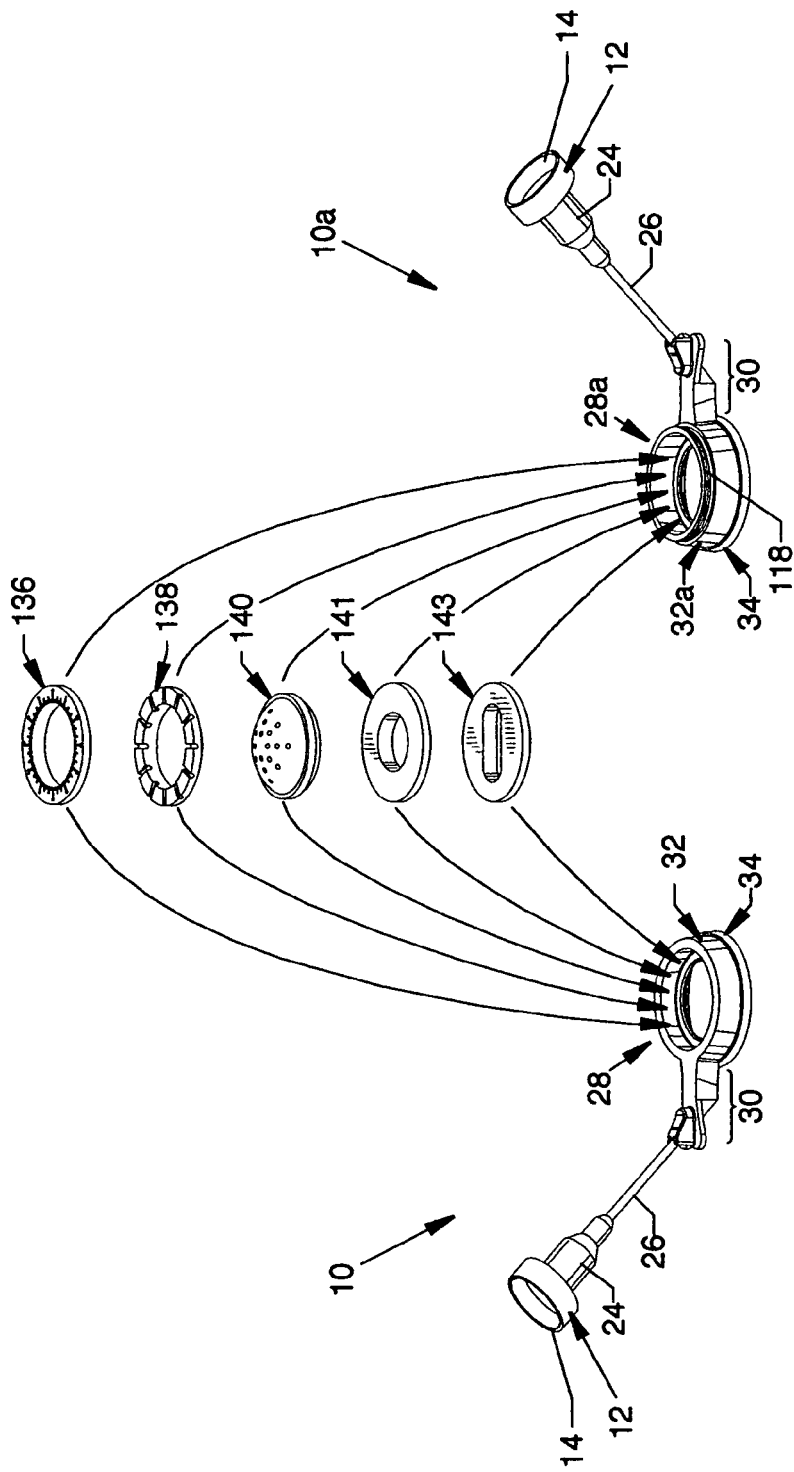
FIG. 19 is an example of a plurality of accompanying closely associated auxiliary devices provided for use with multiple forms of an eye positioner.

FIG. 19 is an example of closely related structures which can complement many of the benefits of the instant invention described in previous figures. An additional plurality of accompanying closely associated auxiliary devices are provided for use with the eye positioner 10 and the eye positioner 10a, some of which include, but which are not limited to, a reference ring 136, a planar surgical instrument guide 138, a domed surgical instrument guide 140, a controlled area guide 141, and an injection guide 143, each of which can be utilized to enhance the operation of the forms of an eye positioner including eye positioner 10 and eye positioner 10a to provide for multiple uses and configurations involving the use of the eye positioners 10 and 10a. FIGS. 19-31 illustrate the configurations and uses of such associated auxiliary devices and various arrangements of such components in conjunction with components of the eye positioner 10, which can also likewise and correspondingly be used with the eye positioner 10a. The reference ring 136, the planar surgical instrument guide 138, the domed surgical instrument guide 140, the controlled area guide 141, and the injection guide 143 each include structure extending from the bottom thereof for accommodation by and for rotation within a portion of the annular open spaces 43 and 43a of the eye positioners 10 and 10a, respectively, where, alternatively, such structure could be flexible, such as by the segmenting of such structure in order to provide for light frictional engagement within a portion of the annular open spaces 43 and 43a. Grooves and mating rings could also be incorporated to provide for releasable and rotatable engagement. Other structure, such as described with respect to FIG. 18, could also be incorporated for positive attachment.

Figure 20:
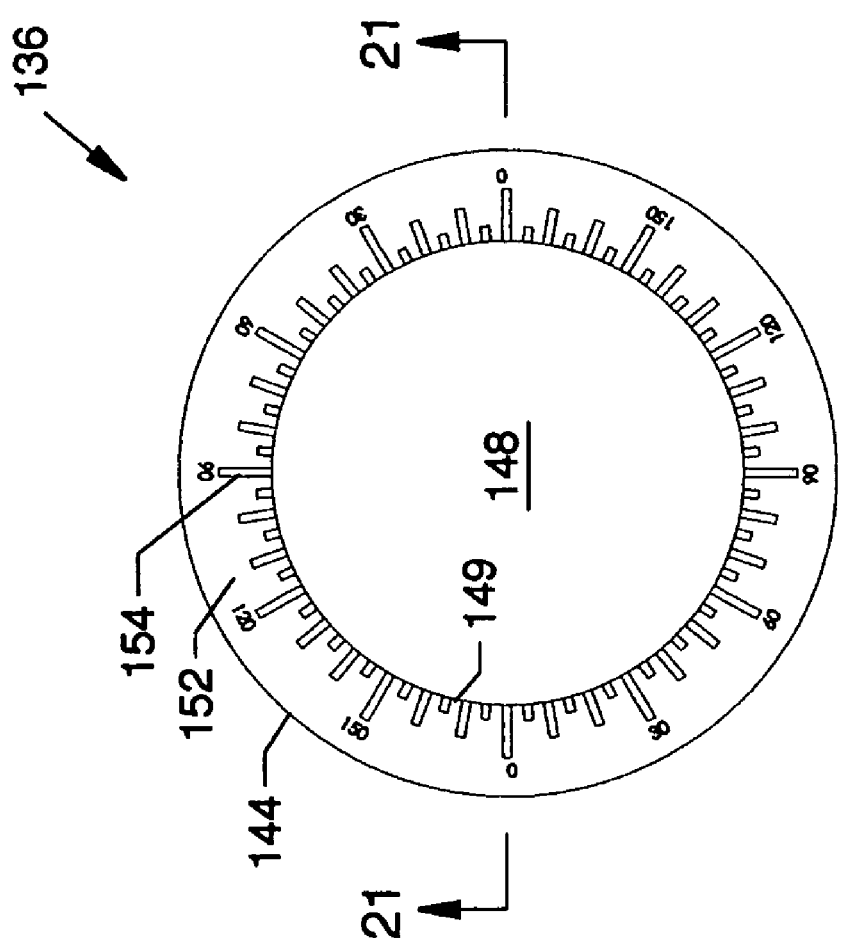
FIG. 20 is a top view of a reference ring.
Figure 21:
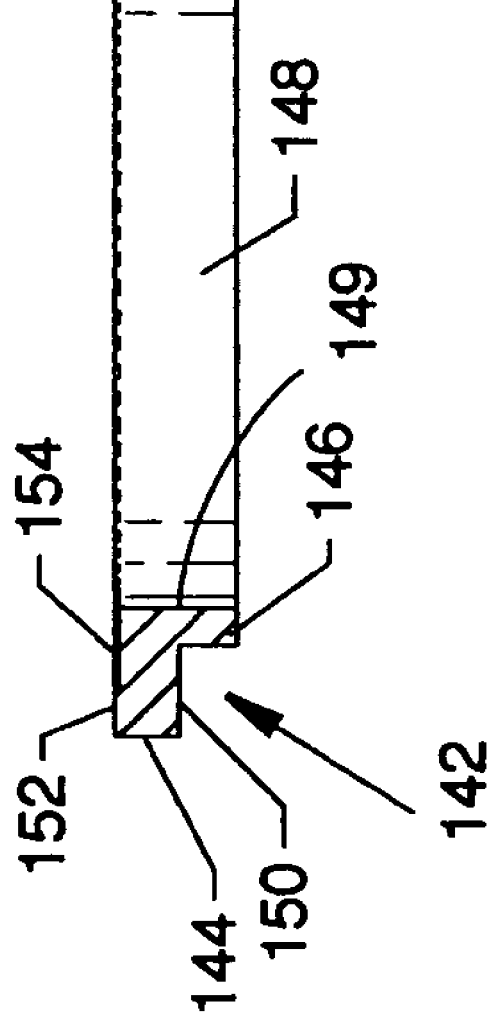
FIG. 21 is a section view of the reference ring along line 21-21 of FIG. 20.

FIG. 20 is a top view of the reference ring 136, and FIG. 21 is a section view of the reference ring 136 along line 21-21 of FIG. 20. With reference to FIGS. 20 and 21, the reference ring 136 is further described. The body of the annularly configured reference ring 136 includes an undercut annular groove 142 at the lower circumferential periphery which delineates a joined annular lip 144 and annular extension 146. An annular open space 148 is included which is bounded by an inner circumferential surface 149 common to the combined structure of the annular lip 144 and annular extension 146. The annular lip 144 also includes an annular bottom surface 150 and also includes an annular top surface 152 upon which reference marks 154 in degrees or other suitable divisions, scales or the like are located. The reference ring 136 can be made of metal, plastic or other suitable material.

Figure 22:
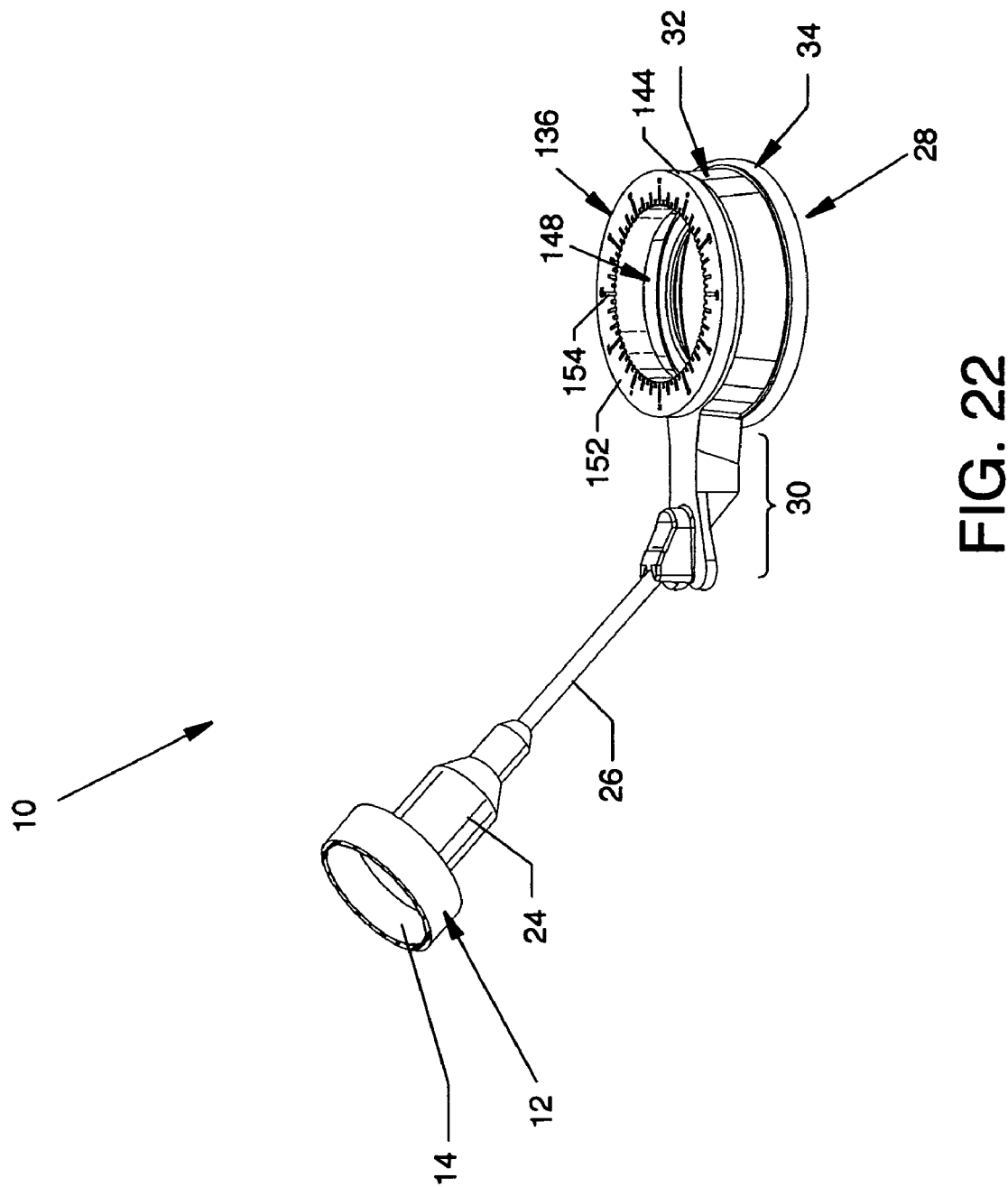
FIG. 22 shows the reference ring engaging the first form of annular vacuum ring.

FIG. 22 shows the reference ring 136 engaging the annular vacuum ring 28.

Figure 23:
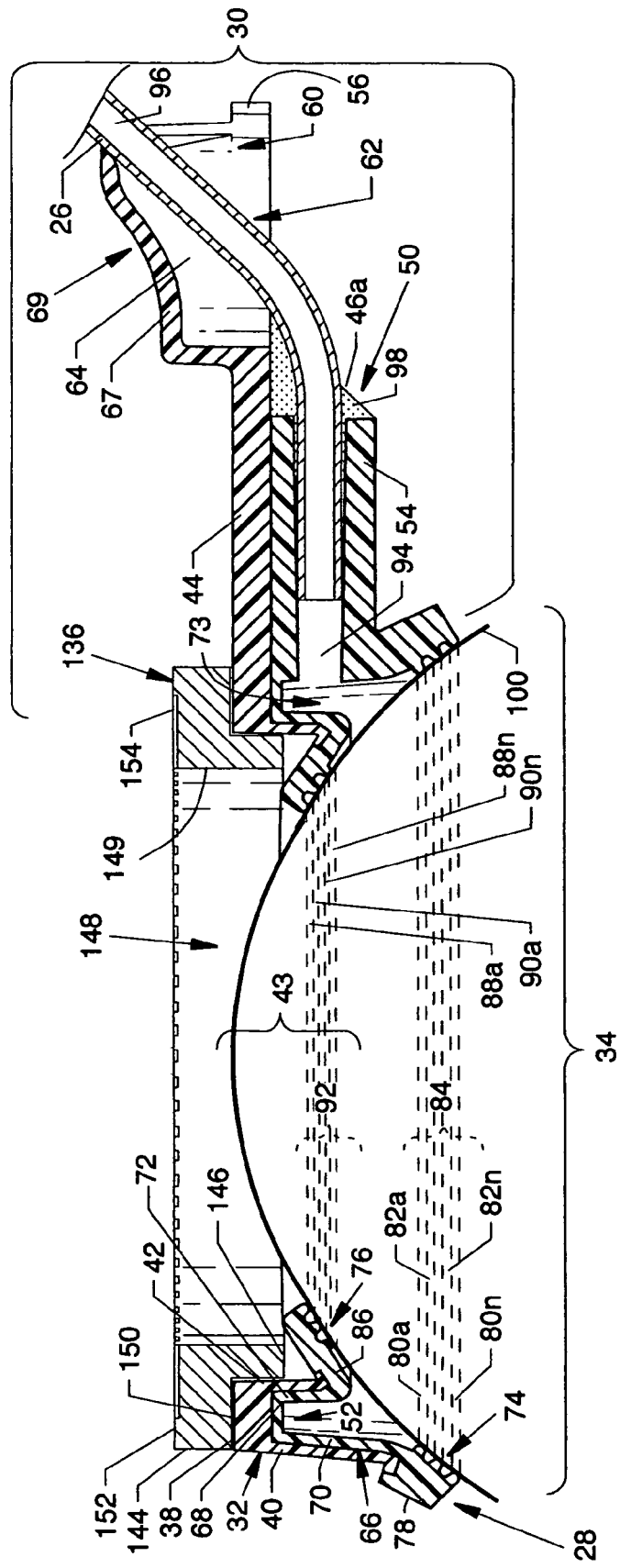
FIG. 23 is a cross section view like FIG. 10 showing the engagement of the reference ring with the first form of annular vacuum ring.

FIG. 23 is a cross section view like FIG. 10 showing the engagement of the reference ring 136 with the annular vacuum ring 28. More specifically, the annular extension 146 of the reference ring 136 is shown in closely coupled accommodation by a portion of the annular open space 43 where the annular extension 146 is closely but rotatably engaged by the inner circumferential panel 42 of the channeled support ring 32. The reference ring 136 can be simply engaged with the annular vacuum ring 28 by aligning the reference ring 136 with the annular vacuum ring 28 and then maneuvering the annular extension 146 into the annular open space 43 until the annular bottom surface 150 of the annular lip 144 stoppingly engages the annular panel 38 of the channeled support ring 32. Manual rotational urging of the reference ring 136 within the annular vacuum ring 28 orients the reference marks 154 on the annular top surface 152 as desired for subsequent referencing of features of the eye 100. In the alternative, a gentle friction fit could be accomplished by the use of tapered structure of the annular extension 146 to gently fix the position of the reference ring 136.

Figure 24:
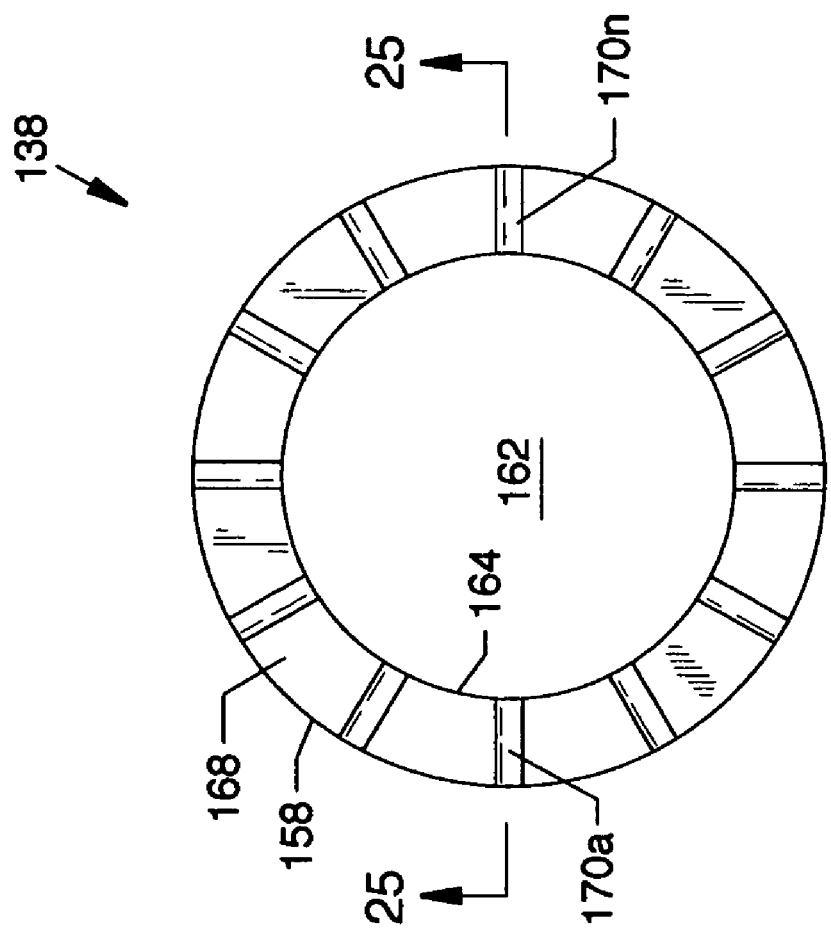
FIG. 24 is a top view of a planar surgical instrument guide.
Figure 25:
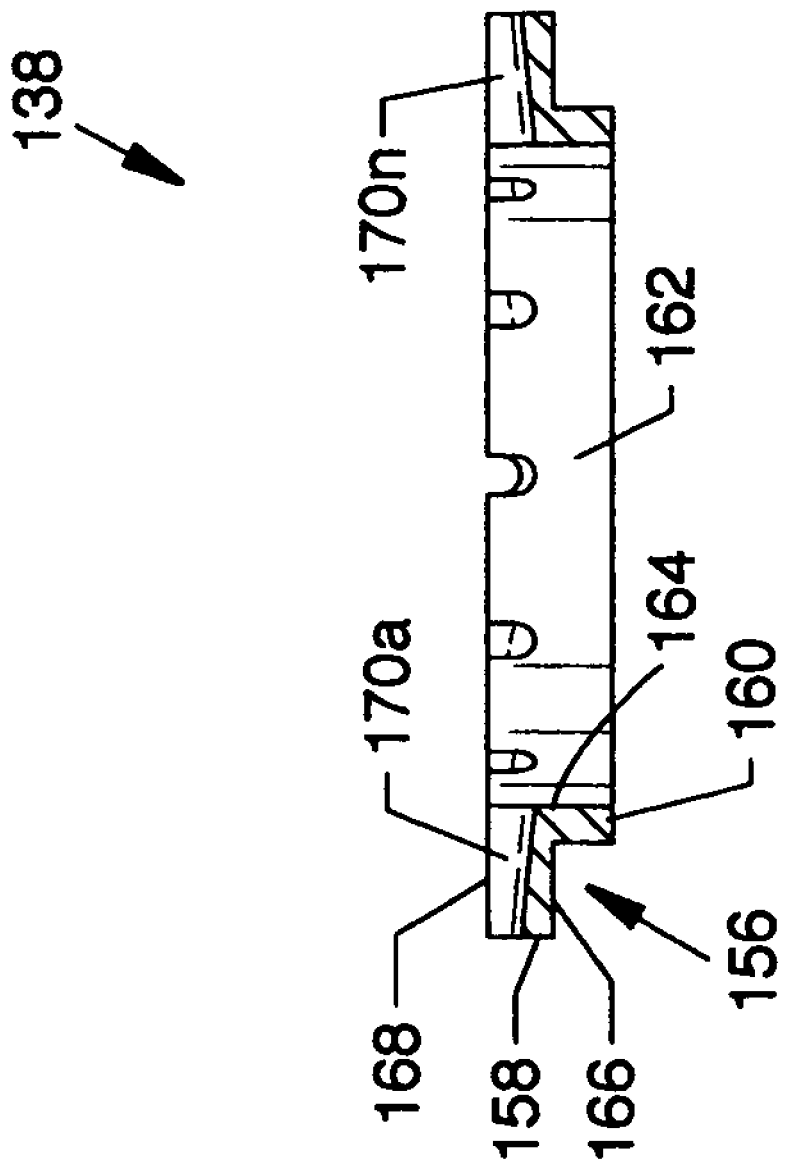
FIG. 25 is a section view of the planar surgical instrument guide along line 25-25 of FIG. 24.

FIG. 24 is a top view of the planar surgical instrument guide 138, and FIG. 25 is a section view of the planar surgical instrument guide 138 along line 25-25 of FIG. 24. With reference to FIGS. 24 and 25, the planar surgical instrument guide 138 is further described. The body of the annularly configured planar surgical instrument guide 138 includes an undercut annular groove 156 at the lower circumferential periphery which delineates a joined annular lip 158 and annular extension 160. An annular open space 162 is included which is bounded by an inner circumferential surface 164 common to the combined structure of the annular lip 158 and the annular extension 160. The annular lip 158 also includes an annular bottom surface 166 and an annular top surface 168. Spaced instrument positioning slots 170a-170n, which can be in a round or other geometrical configuration, are located in radial fashion about the annular top surface 168 for guidance of surgical instruments. The spaced instrument positioning slots 170a-170n are sloped at a common suitable angle toward the annular open space 162; but in the alternative, the angle of the slopes of each of the positioning slots 170a-170n can be a different angle to provide varied angular use of the planar surgical instrument guide 138. Installation and general operation of the planar surgical instrument guide 138 is much the same as previously described where the planar surgical instrument guide 138 can be used in lieu of the reference ring 136, such as shown in FIGS. 22 and 23. The planar surgical instrument guide 138 can be made of metal, plastic or other suitable material.

Figure 26:
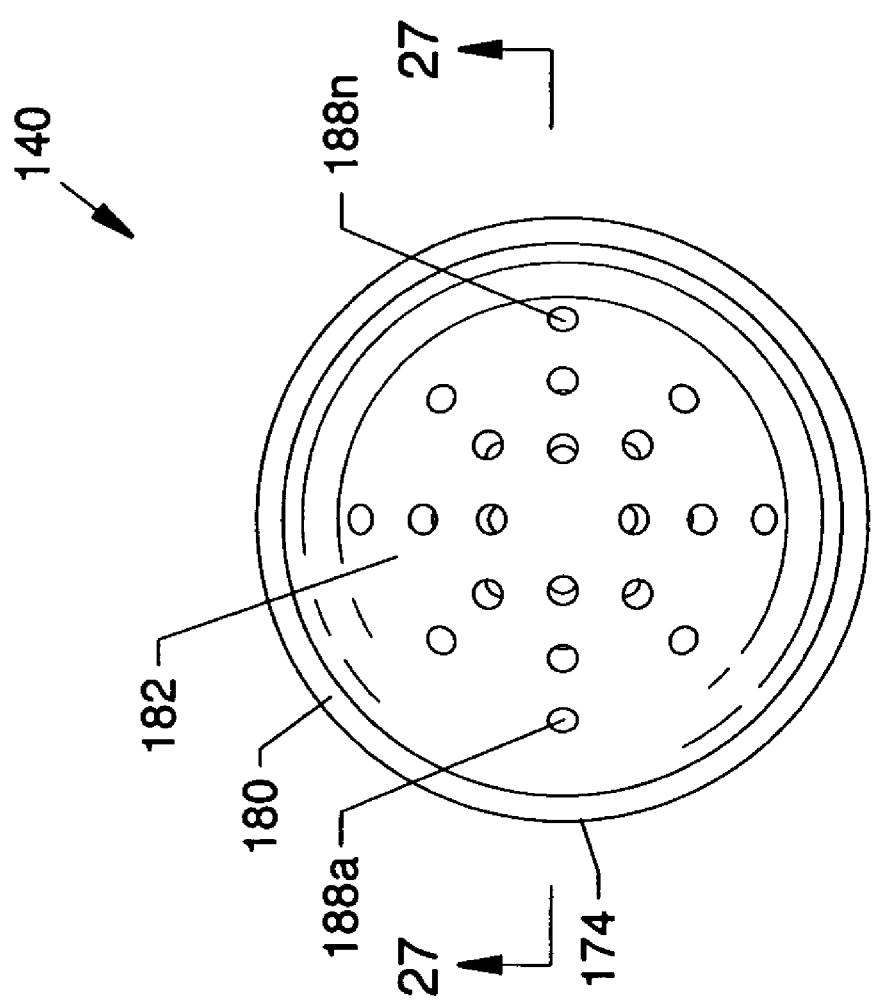
FIG. 26 is a top view of a one-piece domed surgical instrument guide.
Figure 27:
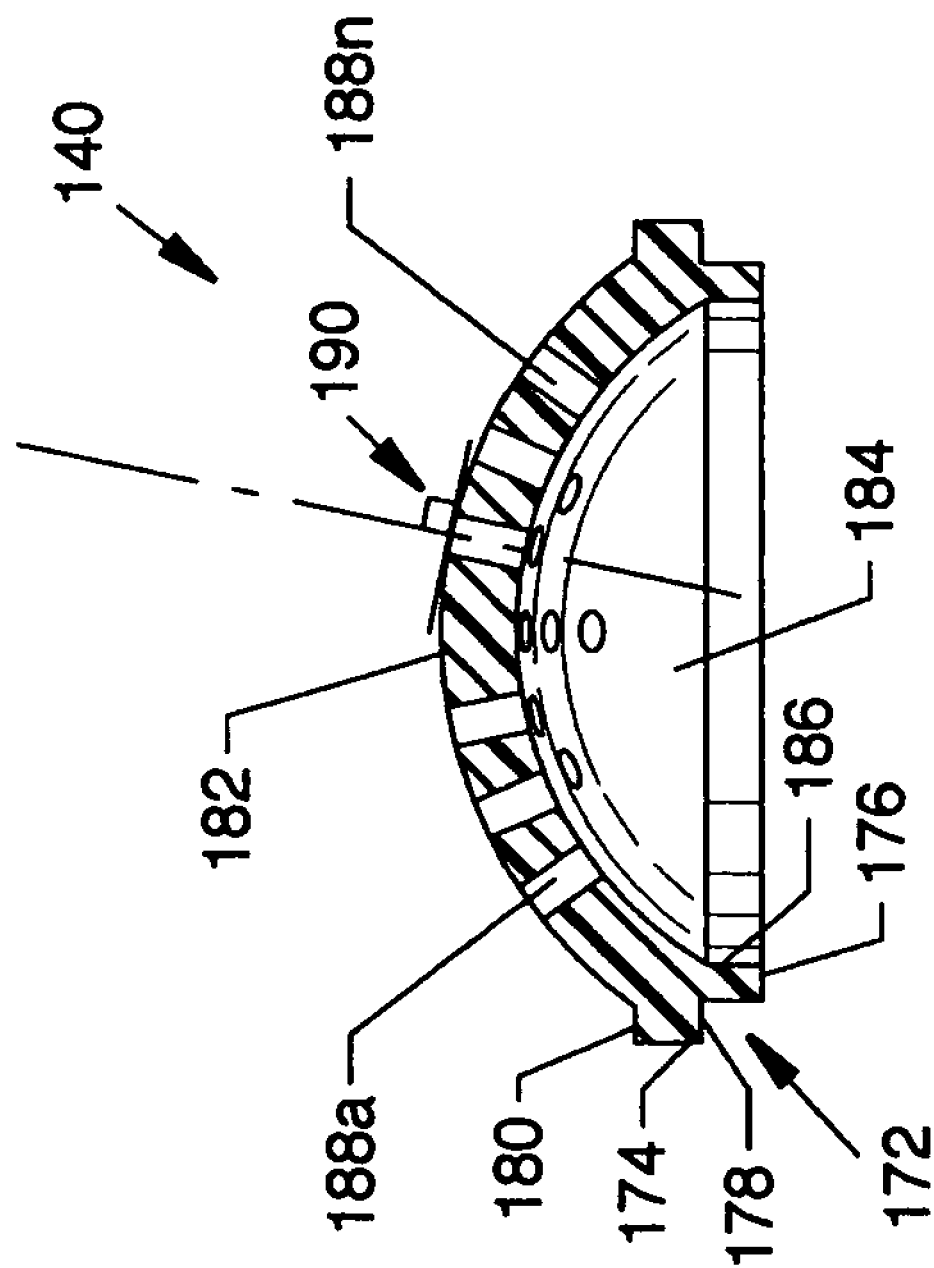
FIG. 27 is a section view of the one-piece domed surgical instrument guide along line 27-27 of FIG. 26.

FIG. 26 is a top view of the one-piece domed surgical instrument guide 140, and FIG. 27 is a section view of the one-piece domed surgical instrument guide 140 along line 27-27 of FIG. 26. With reference to FIGS. 26 and 27, the domed surgical instrument guide 140 is further described. The body of the annularly configured domed surgical instrument guide 140 includes an undercut annular groove 172 at the lower circumferential periphery which delineates a joined annular lip 174 and annular extension 176. The annular lip 174 also includes an annular bottom surface 178 and an annular top surface 180 which is continuous with a top dome 182. An open space 184 is included which is bounded by an inner circumferential surface 186 and by the top dome 182. Spaced instrument positioning holes 188a-188n, which preferably are round but which could be square or of other suitable geometric configuration, are located in radial fashion extending through the top dome 182 for guidance of surgical instruments. The centerlines of each of the spaced instrument positioning holes 188a-188n can be perpendicular to the top dome 182 and directed toward the open space 184 as shown at perpendicular reference 190, but in the alternative, the centerlines of one or more of the spaced instrument positioning holes 188a-188n can be offset from the perpendicular orientation at different angles to provide multiple angular orientations of the instrument positioning holes 188a-188n of the domed surgical instrument guide 140. Installation and general operation of the domed surgical instrument guide 140 is much the same as previously described where the domed surgical instrument guide 140 can be used in lieu of the reference ring 136, such as shown in FIGS. 22 and 23. The domed surgical instrument guide 140 can be made of plastic, metal, or other suitable material.

Figure 28:
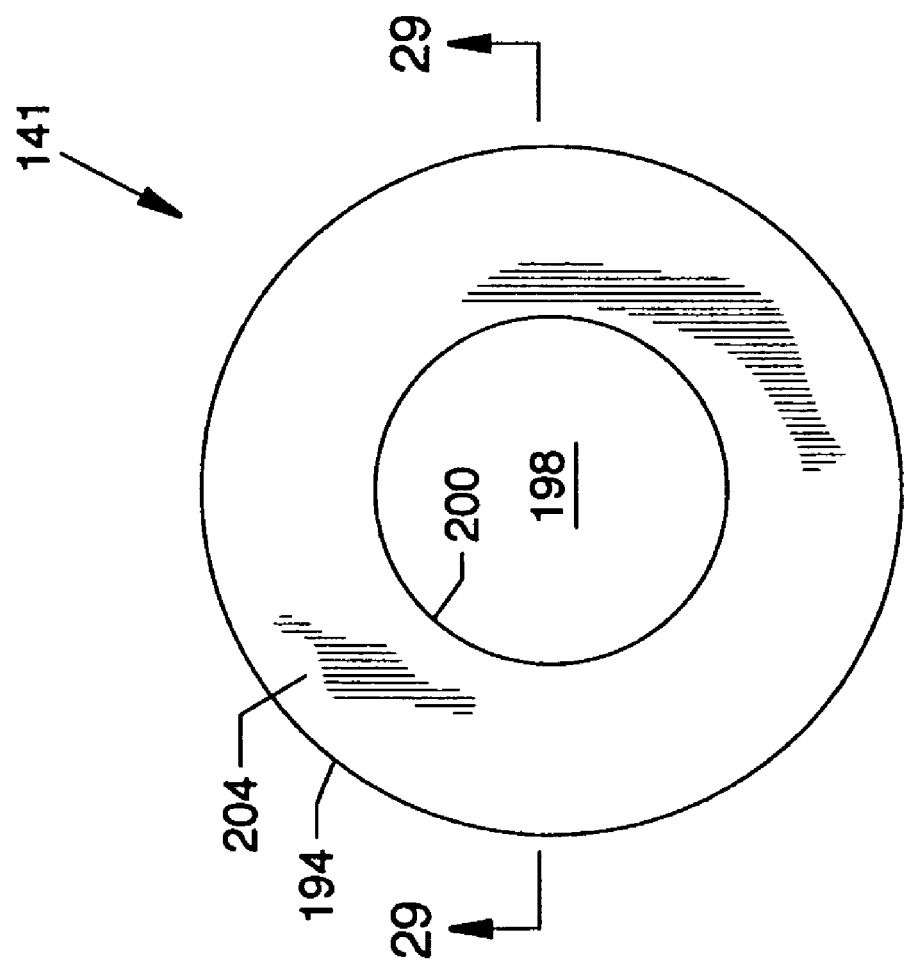
FIG. 28 is a top view of a controlled area guide.
Figure 29:
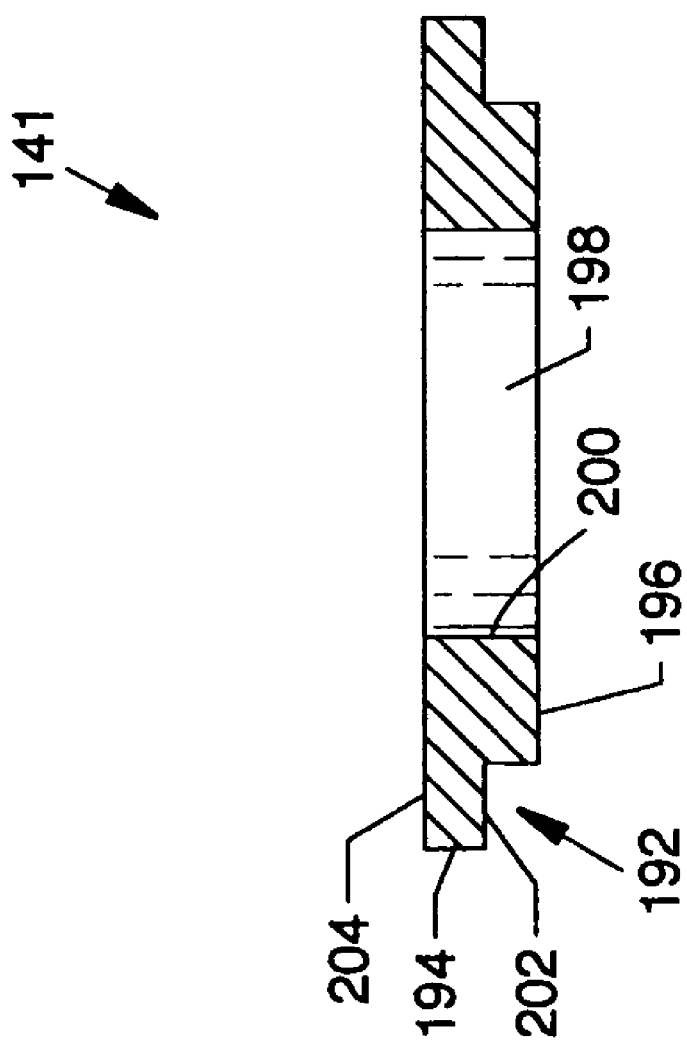
FIG. 29 is a section view of the controlled area guide along line 29-29 of FIG. 28.

FIG. 28 is a top view of the controlled area guide 141, and FIG. 29 is a section view of the controlled area guide 141 along line 29-29 of FIG. 28. With reference to FIGS. 28 and 29, the controlled area guide 141 is further described. The body of the annularly configured controlled area guide 141 includes an undercut annular groove 192 at the lower circumferential periphery which delineates a joined annular lip 194 and annular extension 196. An annular open space 198 is included which is bounded by an inner circumferential surface 200 common to the combined structure of the annular lip 194 and the annular extension 196. The annular lip 194 also includes an annular bottom surface 202 and an annular top surface 204. The annular open space 198 is used for procedures where contact with the eye 100 is to be limited or contained within a finite area, such as that defined by the diameter of the annular open space 198. The controlled area guide 141 can be made of metal, plastic, or other suitable material.

Figure 30:
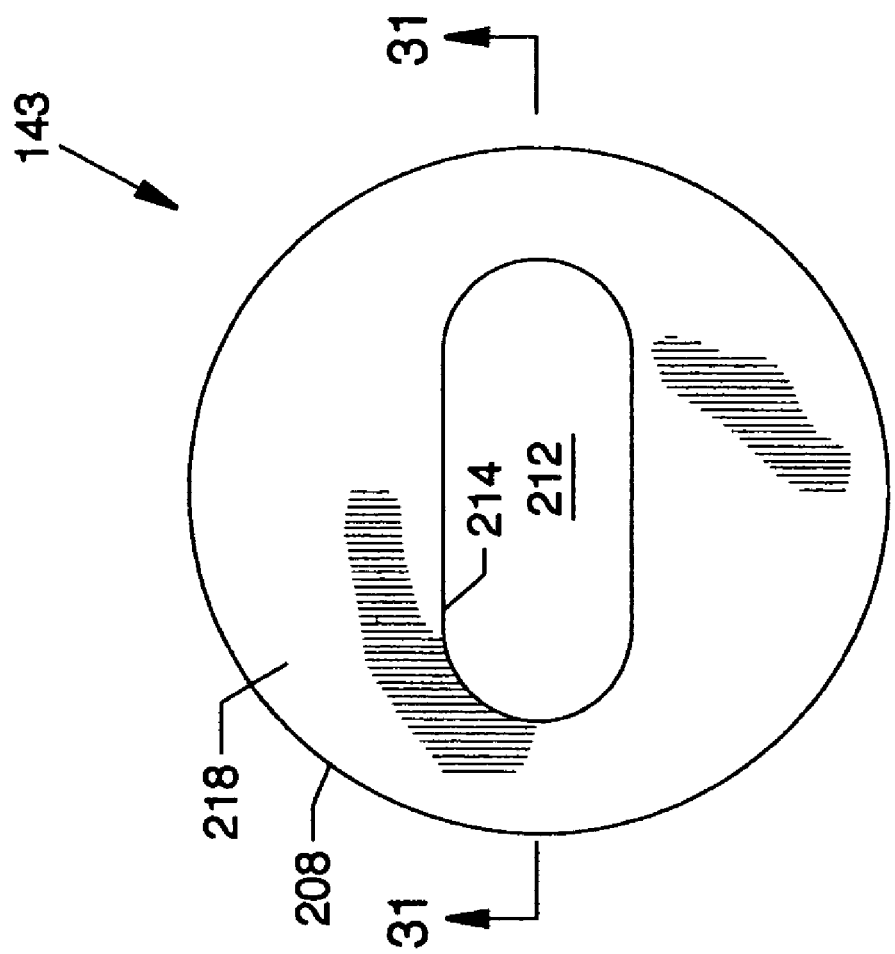
FIG. 30 is a top view of an injection guide.
Figure 31:
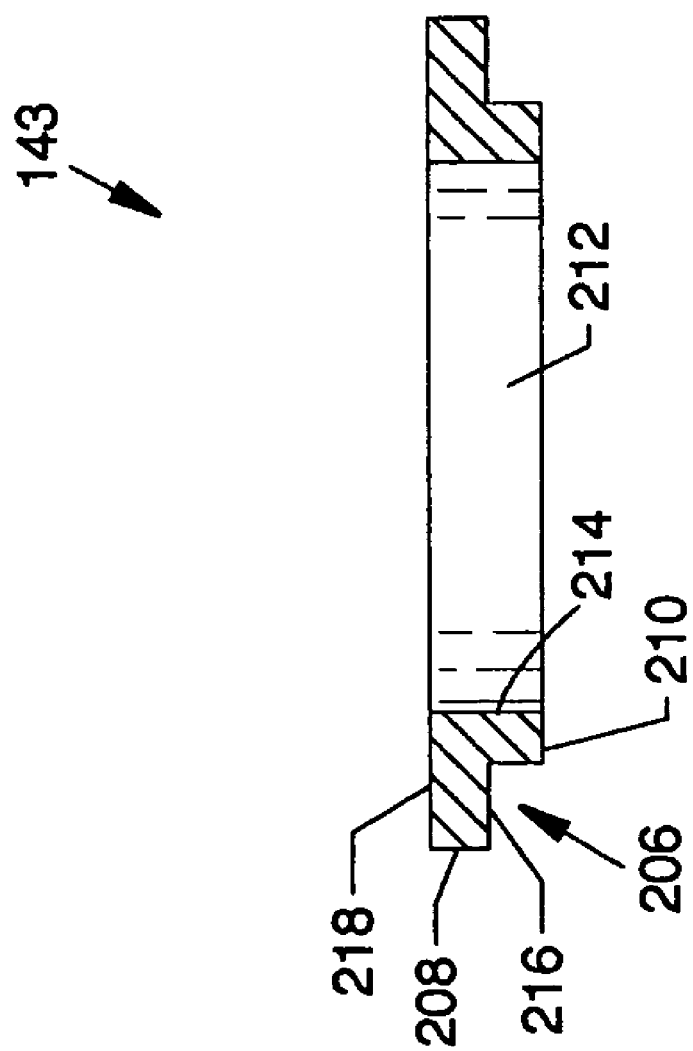
FIG. 31 is a section view of the injection guide along line 31-31 of FIG. 30.

FIG. 30 is a top view of the injection guide 143, and FIG. 31 is a section view of the injection guide 143 along line 31-31 of FIG. 30. With reference to FIGS. 30 and 31, the injection guide 143 is further described. The body of the annularly configured injection guide 143 includes an undercut annular groove 206 at the lower circumferential periphery which delineates a joined annular lip 208 and annular extension 210. A slot 212, which is an open space, is included and bounded by an inner slot surface 214 common to the combined structure of the annular lip 208 and the annular extension 210. The annular lip 208 also includes an annular bottom surface 216 and an annular top surface 218. In the alternative, the slot 212 can be of other shapes, such as, but not limited to, elliptical, oval, round, or other convenient geometrical shape. Also, the periphery of the injection guide 143 could be shaped to conform to other forms of vacuum rings, which could be oval, elliptical, or even of other geometric configuration. The slot 212 is used for procedures to provide a small mini-sterile field for intraocular injections into the vitreous for surgeries, such as vitreous injections of agents directed toward macular degeneration. Current asepsis and stabilization of the eye is inadequate and the injection guide 143, which is slightly enlarged with respect to the reference ring 136, the planar instrument guide 138, the domed instrument guide 140, and the controlled area guide 141, is best used with a slightly enlarged annular vacuum ring 28 or 28*a* to provide exposure of the area of the eye at 3-4 mm from the limbus. The injection guide 143 can be made of metal, plastic, or other suitable material.

In conclusion, it should be understood that present invention, without limitation, in one preferred embodiment is a self-contained handheld eye positioner. The eye positioner includes an annular vacuum ring having a flexible sealing ring mated to a rigid channeled support ring, an attachment fixture having a rigid receptacle extending from the rigid channeled support ring of the annular vacuum ring and a flexible housing extending from the flexible sealing ring, the flexible housing including a bore through the flexible housing for communication with the annular vacuum ring, accommodated within the receptacle, and a rigid hollow tube affixed within the attachment fixture by insertion into the bore of the flexible housing and extending therefrom to a connector so as to provide a connection for communication to the annular vacuum ring and serve as a handle relative to the annular vacuum ring. More preferably, the flexible sealing ring of the annular vacuum ring is mated to the rigid channeled support ring by a method selected from the group consisting of overmolding the flexible sealing ring to the rigid channeled support ring, adhesive bonding of the flexible sealing ring to the rigid channeled support ring, ultrasonic welding of the flexible sealing ring to the rigid channeled support ring, and compression fit of the flexible sealing ring to the rigid channeled support ring. Preferably, the connector of the rigid hollow tube is a Luer connector. Preferably, a syringe is attached to the Luer connector, the syringe functioning both as a vacuum source and as a rigid handle extension relative to the unitary annular vacuum ring. Preferably, the rigid receptacle of the attachment fixture includes an engagement channel and a connecting narrower restrictive access channel, the narrower restrictive access channel defined by at least one resiliently flexible member of the rigid receptacle. This allows for forcible accommodation of the rigid tube when inserted into the bore of the flexible housing of the attachment fixture. This forcible accommodation may be to snappingly engage the rigid tube with the rigid receptacle and the bore of the flexible housing is tapered. Alternatively, the rigid tube engages by compression of or with the rigid receptacle. Preferably, the rigid channeled support ring also serves as a substrate support ring. As a substrate support ring, it serves to provide a means for aligned securement of geometrically configured auxiliary devices to the rigid channeled substrate support ring. This can be by threaded attachment, bayonet attachment, ring and groove attachment, friction fit, adhesive attachment, slotted member attachment, light bulb-to-socket slotted type engagement, and/or tongue and groove attachment. This attachment allows for an insert to be selected to facilitate medical or visual treatment of the eye. In another preferred embodiment, the present invention is a method of manufacturing an eye positioner. In the method, a rigid channeled support with a rigid receptacle extending therefrom is provided. A flexible sealing ring and housing is overmolded to the rigid channeled support and rigid receptacle. Preferably, the method also provides a rigid tube and engaging the housing with the rigid tube to establish communication with the overmolded flexible sealing ring. In another preferred embodiment, the present invention is a method of positioning an eye. In the method, a self-contained handheld eye positioner with an annular vacuum ring including a flexible sealing ring mated to a rigid channeled support, attachment fixture, rigid tube, and syringe vacuum source is provided. This is employed to engage the eye and a vacuum is generated with the syringe to cause the eye to be grasped, maneuvered and suitably positioned by the self-contained handheld eye positioner. Again, inserts can be provided and accommodated and aligned and secured to the annular vacuum ring. The inserts, whether secured before or after engaging the eye, are in an aligned relationship to the rigid channeled support, such that the insert and the eye become aligned. These inserts can cause reshaping of the eye. These inserts can cause diffusion, blocking, focusing or filtering of radiation subsequently applied to the eye, where the radiation is sound, light, laser, and electromagnetic energy radiation. Thus, without limiting the present invention, the advantages of such can be appreciated.

Various modifications can be made to the present invention without departing from the apparent scope thereof.

PARTS LIST

10 eye positioner
10*a* eye positioner
11 general structure
12 instrument handle
14 syringe
16 syringe plunger shaft
18 spring
20 syringe plunger shaft planar member
22 grasping tab
25 Luer adapter
25 internally threaded end
26 rigid hollow tube
28 annular vacuum ring
28*a* annular vacuum ring
30 attachment fixture 32 channeled support ring
32a channeled support ring
34 flexible sealing ring
38 annular panel
38a annular panel
39 arcuate lip
40 outer circumferential arcuate panel
41 annular lip
42 inner circumferential panel
42a inner circumferential panel
43 annular open space
43a annular open space
44 planar panel extension
46 panel
46a arcuate panel end
48 panel
48a arcuate panel end
50 receptacle
52 annular channel
54 housing
56 arcuate section
58 arcuate section
60 restrictive access channel
62 engagement channel
64 stabilizer panel
65 stabilizer panel
66 annular connecting seal
67 top panel
68 annular panel
69 receptor enclosure
70 outer circumferential side
72 inner circumferential side
73 annular vacuum channel
74 outer flexible sealing array
76 inner flexible sealing array
78 outwardly angled side portion
80a-n eye contact rings
81 outer annular channel
82a-n grooves
84 annular open space
86 annular panel
87 inner annular channel
88a-n eye contact rings
90a-n grooves
92 annular open space
94 tapered bore
96 lumen
98 adhesive
100 eye
102 flexible tube
104 Luer connector
106 Luer connector
108 stopcock
110 Luer adaptor
112 plano-plano lens
114 plano-concave lens
116 plano-convex lens
118 threaded fixture
120 planar top
122 circumferential side
124 threads
126 extension
128 planar surface
130 annular space
132 concave surface
134 convex surface
136 reference ring
138 planar surgical instrument guide
140 domed surgical instrument guide
141 controlled area guide
142 annular groove
143 injection guide
144 annular lip
146 annular extension
148 annular open space
149 inner circumferential surface
150 annular bottom surface
152 annular top surface
154 reference marks
156 annular groove
158 annular lip
160 annular extension
162 annular open space
164 inner circumferential surface
166 annular bottom surface
168 annular top surface
170a-n instrument positioning slots
172 annular groove
174 annular lip
176 annular extension
178 annular bottom surface
180 annular top surface
182 top dome
184 open space
186 inner circumferential surface
188a-n instrument positioning holes
190 perpendicular reference
192 annular groove
194 annular lip
196 annular extension
198 annular open space
200 inner circumferential surface
202 annular bottom surface
204 annular top surface
206 annular groove
208 annular lip
210 annular extension
212 slot
214 inner slot surface
216 annular bottom surface
218 annular top surface It is claimed:
1. A self-contained handheld eye positioner, comprising:
 a. an annular vacuum ring, the vacuum ring including a flexible sealing ring and a rigid channeled support ring, the flexible sealing ring formed of a flexible material, and mated to the rigid channeled support ring, the rigid channeled support ring formed of a rigid material distinct from the flexible material of the flexible sealing ring mated thereto such that a unitary, integral structure is presented;
 b. an attachment fixture having a rigid receptacle integral with and extending from the rigid channeled support ring of the annular vacuum ring;
 c. a flexible housing integral with and extending from the flexible sealing ring, the flexible housing including a bore through the flexible housing for communication with the annular vacuum ring, wherein the flexible housing is accommodated within the receptacle; and,
 c. a rigid hollow tube affixed within the attachment fixture by insertion into the bore of the flexible housing and extending therefrom to a connector so as to provide a connection for communication to the annular vacuum ring and serve as a handle relative to the annular vacuum ring.

2. The self-contained handheld eye positioner of claim 1, wherein the connector of the rigid hollow tube is a Luer connector.

3. The self-contained handheld eye positioner of claim 2, further comprising:
   a. a syringe attached to the Luer connector, the syringe functioning as a vacuum source and as a rigid handle extension relative to the unitary annular vacuum ring.

4. The self-contained handheld eye positioner of claim 1, wherein the flexible sealing ring of the annular vacuum ring is mated to the rigid channeled support ring by a method selected from the group consisting of overmolding the flexible sealing ring to the rigid channeled support ring, adhesive bonding of the flexible sealing ring to the rigid channeled support ring.

5. The self-contained handheld eye positioner of claim 1, wherein the rigid receptacle of the attachment fixture includes an engagement channel and a connecting narrower restrictive access channel, the narrower restrictive access channel defined by at least one resiliently flexible member of the rigid receptacle and allowing forcible accommodation of the rigid tube when inserted into the bore of the flexible housing of the attachment fixture.

6. The self-contained handheld eye positioner of claim 5, wherein the rigid tube snappingly engages with the rigid receptacle and the bore of the flexible housing is tapered.

7. The self-contained handheld eye positioner of claim 5, wherein the rigid tube engages by compression with the rigid receptacle and the bore of the flexible housing is tapered.

8. The self-contained handheld eye positioner of claim 2, further comprising:
   a. a flexible tube extending from the Luer connector, the flexible tube adapted for connection to a vacuum source; and,
   b. a valve controlling communications between the vacuum source and the annular vacuum ring.

9. The self-contained handheld eye positioner of claim 1, wherein the rigid channeled support ring further includes:
   a. means for aligned securement of geometrically configured auxiliary devices to the rigid channeled support ring.

10. The self-contained handheld eye positioner of claim 9, wherein the means for aligned securement is selected from the group consisting of threaded attachment, bayonet attachment, ring and groove attachment, slotted member attachment, and light bulb-to-socket type engagement.

11. The self-contained handheld eye positioner of claim 1, wherein the rigid channeled support ring also serves as a substrate support ring and the substrate support ring further includes:
   a. means for aligned securement of geometrically configured auxiliary devices to the rigid channeled substrate support ring.

12. The self-contained handheld eye positioner of claim 11, wherein the means for aligned securement is selected from the group consisting of threaded attachment, bayonet attachment, ring and groove attachment, friction fit, adhesive attachment, slotted member attachment, light bulb-to-socket slotted type engagement, and tongue and groove attachment.

13. A self-contained handheld eye positioner, comprising:
   a. an annular vacuum ring, the vacuum ring including a flexible sealing ring and a rigid channeled support ring, the flexible sealing ring formed of a flexible material, and mated to the rigid channeled support ring, the rigid channeled support ring formed of a rigid material distinct from the flexible material of the flexible sealing ring mated thereto such that a unitary structure is presented;
   b. an attachment fixture having a rigid receptacle extending from the rigid channeled support ring of the annular vacuum ring
   c. a flexible housing extending from the flexible sealing ring, the flexible housing including a bore through the flexible housing for communication with the annular vacuum ring, wherein the flexible housing is accommodated within the receptacle; and,
   c. a rigid hollow tube affixed within the attachment fixture by insertion into the bore of the flexible housing and extending therefrom to a connector so as to provide a connection for communication to the annular vacuum ring and serve as a handle relative to the annular vacuum ring.

\* \* \* \* \*